(12) United States Patent
Totz

(10) Patent No.: US 7,921,847 B2
(45) Date of Patent: Apr. 12, 2011

(54) DEVICE AND METHOD FOR PLACING WITHIN A PATIENT AN ENTERAL TUBE AFTER ENDOTRACHEAL INTUBATION

(75) Inventor: Kenneth A. Totz, Houston, TX (US)

(73) Assignee: Intubix, LLC, Houston, TX (US)

( * ) Notice: Subject to any disclaimer, the term of this patent is extended or adjusted under 35 U.S.C. 154(b) by 1633 days.

(21) Appl. No.: 11/188,821

(22) Filed: Jul. 25, 2005

(65) Prior Publication Data

US 2007/0017527 A1    Jan. 25, 2007

(51) Int. Cl.
*A61M 16/00*  (2006.01)
*A61M 31/00*  (2006.01)
*A61M 29/00*  (2006.01)
*A61M 25/00*  (2006.01)
*A61M 27/00*  (2006.01)

(52) U.S. Cl. ......... 128/207.15; 128/200.26; 128/207.14; 128/207.16; 604/101.01; 604/101.04; 606/192; 606/194; 606/196

(58) Field of Classification Search ............. 128/207.14, 128/207.15, 207.16, 200.26; 604/94.01, 604/96.01, 101.01, 101.04, 264, 284, 523, 604/544; 606/192–196
See application file for complete search history.

(56) References Cited

U.S. PATENT DOCUMENTS

| | | | |
|---|---|---|---|
| 3,625,793 A | 12/1971 | Sheridan |
| 4,023,596 A | 5/1977 | Tate |
| 4,090,518 A | 5/1978 | Elam |
| 4,167,946 A | 9/1979 | Sandstrom |
| 4,231,365 A | 11/1980 | Scarberry |
| 4,233,984 A | 11/1980 | Walling |
| 4,256,099 A | 3/1981 | Dryden |
| 4,327,720 A | 5/1982 | Bronson et al. |
| 4,351,330 A | 9/1982 | Scarberry |
| 4,453,545 A | 6/1984 | Inoue |
| 4,584,998 A | 4/1986 | McGrail |
| 4,672,960 A | 6/1987 | Frankel |

(Continued)

FOREIGN PATENT DOCUMENTS

DE    19533615    4/1997

(Continued)

OTHER PUBLICATIONS

Hook and loop reclosable cable tie wraps. 2-page printout from the website catalog of levitonproducts.com.

(Continued)

*Primary Examiner* — Patricia M Bianco
*Assistant Examiner* — Nihir Patel
(74) *Attorney, Agent, or Firm* — Gordon G. Waggett, P.C.

(57) ABSTRACT

The present invention is directed to a novel device and method for providing a disposable endotracheal intubation device for use with an auxiliary passageway serving as a guide for the placement of an orogastic or other enterally directed device in a patient. The present invention pertains to a combination intubation device comprising an endotracheal tube and a catheter proximate the endotracheal tube to guide the path of an enteral tube. In a preferred embodiment, the endotracheal tube is capable of defining an arcuate path in a first geometric plane between its proximal end and its distal end to facilitate introduction of the tube into the trachea of a patient. In a preferred embodiment, the catheter employs a fenestration to facilitate removal of the intubation device from the patient without removal of any enteral device previously directed therethrough into the patient.

75 Claims, 13 Drawing Sheets

U.S. PATENT DOCUMENTS

| | | |
|---|---|---|
| 4,774,945 A | 10/1988 | White et al. |
| 4,840,172 A | 6/1989 | Augustine et al. |
| 4,840,173 A | 6/1989 | Porter, III |
| 5,009,227 A | 4/1991 | Nieuwstad |
| 5,038,766 A | 8/1991 | Parker |
| 5,065,755 A | 11/1991 | Klafta |
| 5,067,497 A | 11/1991 | Greear et al. |
| 5,069,206 A | 12/1991 | Crosbie |
| 5,143,062 A | 9/1992 | Peckham |
| 5,253,643 A | 10/1993 | Price |
| 5,287,848 A | 2/1994 | Cubb et al. |
| 5,353,787 A | 10/1994 | Price |
| 5,372,131 A | 12/1994 | Heinen, Jr. |
| 5,499,625 A | 3/1996 | Frass et al. |
| 5,520,175 A | 5/1996 | Fry |
| 5,551,421 A | 9/1996 | Noureldin et al. |
| 5,551,946 A | 9/1996 | Bullard |
| 5,588,424 A | 12/1996 | Insler et al. |
| 5,660,175 A | 8/1997 | Dayal |
| 5,665,052 A | 9/1997 | Bullard |
| 5,682,880 A | 11/1997 | Brain |
| 5,694,929 A | 12/1997 | Christopher |
| 5,827,227 A | 10/1998 | DeLago |
| 5,878,745 A | 3/1999 | Brain |
| 5,957,134 A | 9/1999 | Lee |
| 5,964,217 A | 10/1999 | Christopher |
| 6,142,144 A | 11/2000 | Pacey |
| 6,374,827 B1 | 4/2002 | Bowden et al. |
| 6,439,232 B1 | 8/2002 | Brain |
| 6,443,156 B1 | 9/2002 | Niklason et al. |
| 6,460,540 B1 * | 10/2002 | Klepper ................... 128/207.14 |
| 6,461,363 B1 | 10/2002 | Gadberry et al. |
| 6,513,527 B1 | 2/2003 | Abdel-Aziz |
| 6,520,183 B2 | 2/2003 | Amar |
| 6,543,446 B1 | 4/2003 | Christopher |
| 6,543,447 B2 | 4/2003 | Pacey |
| 6,568,388 B2 | 5/2003 | Christopher |
| 6,626,169 B2 | 9/2003 | Gaitini |
| 6,631,713 B1 | 10/2003 | Christopher |
| 6,655,377 B2 | 12/2003 | Pacey |
| 6,718,970 B2 | 4/2004 | Sniadach |
| 6,729,325 B2 | 5/2004 | Alfery |
| 6,843,250 B2 | 1/2005 | Efrati |
| 6,860,264 B2 | 3/2005 | Christopher |
| 6,923,176 B2 | 8/2005 | Ranzinger |
| 7,013,899 B2 | 3/2006 | Alfery et al. |
| 7,040,322 B2 | 5/2006 | Fortuna |
| RE39,508 E | 3/2007 | Parker |
| 7,201,168 B2 | 4/2007 | McGrail et al. |
| 7,278,420 B2 | 10/2007 | Ganesh et al. |
| 7,305,985 B2 | 12/2007 | Brain |
| 2001/0054425 A1 | 12/2001 | Bertram |
| 2003/0051734 A1 | 3/2003 | Brain |
| 2003/0062039 A1 | 4/2003 | Sniadach |
| 2003/0183234 A1 | 10/2003 | Ranzinger |
| 2004/0000314 A1 | 1/2004 | Angel |
| 2004/0020491 A1 | 2/2004 | Fortuna |
| 2004/0111069 A1 | 6/2004 | Schaaf et al. |
| 2005/0039754 A1 * | 2/2005 | Simon ..................... 128/207.14 |
| 2005/0090712 A1 | 4/2005 | Cubb |
| 2005/0137614 A1 | 6/2005 | Porter et al. |
| 2006/0090761 A1 | 5/2006 | Kurrus |
| 2006/0166548 A1 | 7/2006 | Williams et al. |
| 2007/0106117 A1 | 5/2007 | Yokota |
| 2007/0106121 A1 | 5/2007 | Yokota et al. |
| 2007/0106122 A1 | 5/2007 | Yokota et al. |
| 2007/0163596 A1 | 7/2007 | Mikkaichi et al. |
| 2007/0221229 A1 | 9/2007 | Rahaghi et al. |
| 2007/0244546 A1 | 10/2007 | Francis |
| 2008/0000481 A1 | 1/2008 | Ganesh et al. |
| 2008/0060655 A1 | 3/2008 | Brain |
| 2008/0135052 A1 | 6/2008 | Bussieres |
| 2008/0142017 A1 | 6/2008 | Brain |
| 2008/0146879 A1 | 6/2008 | Pacey |

FOREIGN PATENT DOCUMENTS

| | | |
|---|---|---|
| EP | 0 230 790 | 8/1987 |
| JP | 2002-315832 | 10/2002 |

OTHER PUBLICATIONS

Prior Art described in Specification paragraphs [0072]-[0073] Fig. 1.
Adjustable Nylon Ratchet Clamps. 3-page printout from the website catalog of ElectricalBasics.com.
Related PCT Application: PCT/US2010/020082 (filed Jan. 5, 2010, directed to U.S. Appl. No. 12/352,404, CIP of present application): PCT Notification of Transmittal of the International Search Report and the Written Opinion of the International Searching Authority, or the Declaration (Aug. 13, 2010)(2 pages).
Related PCT Application: PCT/US2010/020082 (filed Jan. 5, 2010, directed to U.S. Appl. No. 12/352,404, CIP of present application): PCT International Search Report (Aug. 13, 2010)(4 pages).
Related PCT Application: PCT/US2010/020082 (filed Jan. 5, 2010, directed to U.S. Appl. No. 12/352,404, CIP of present application): PCT Written Opinion of the International Searching Authority (Aug. 13, 2010)(4 pages).
Netter, Frank H., M.D., (Sharon Colacino, Consulting Ed.), "Atlas of Human Anatomy", (1989), Plate 57, Ciba-Geigy Corporation, Summit, New Jersey.

* cited by examiner

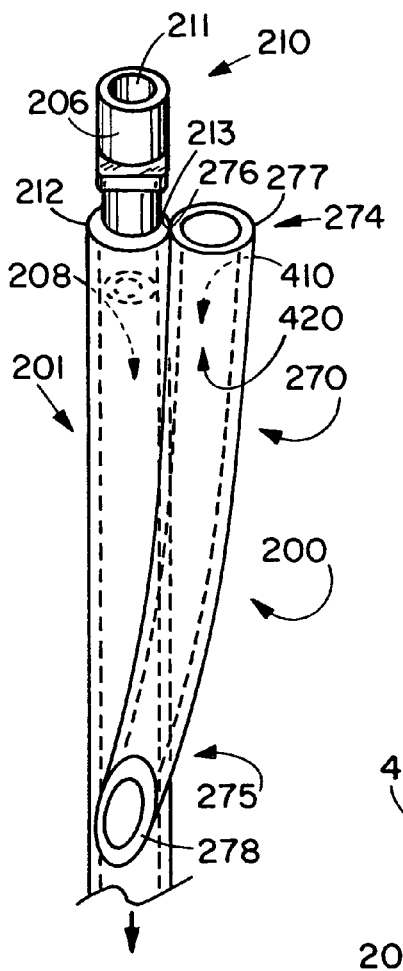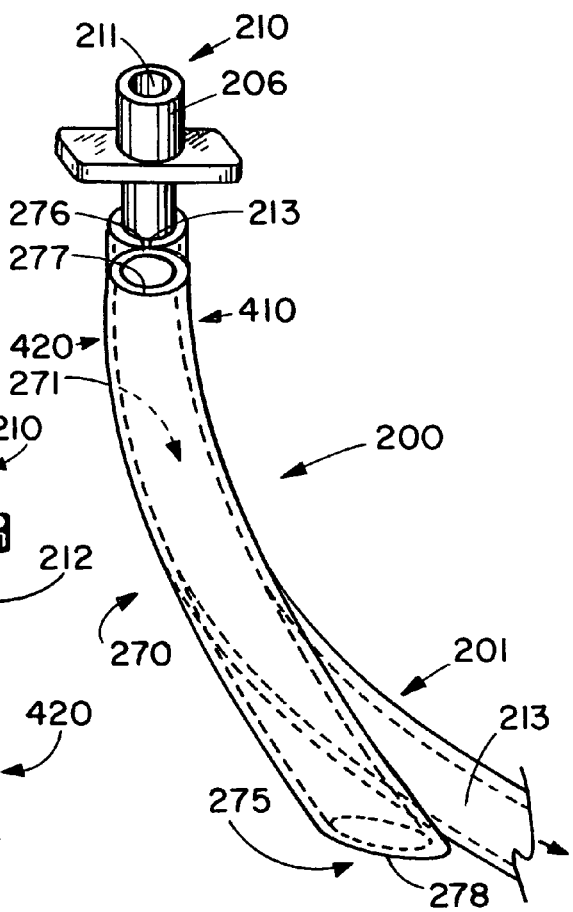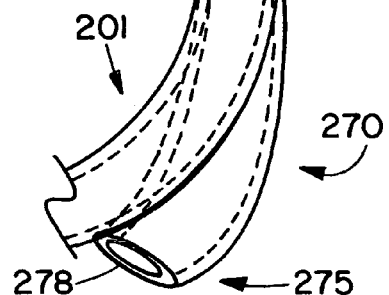
Fig. 2c
Fig. 2b
Fig. 2d

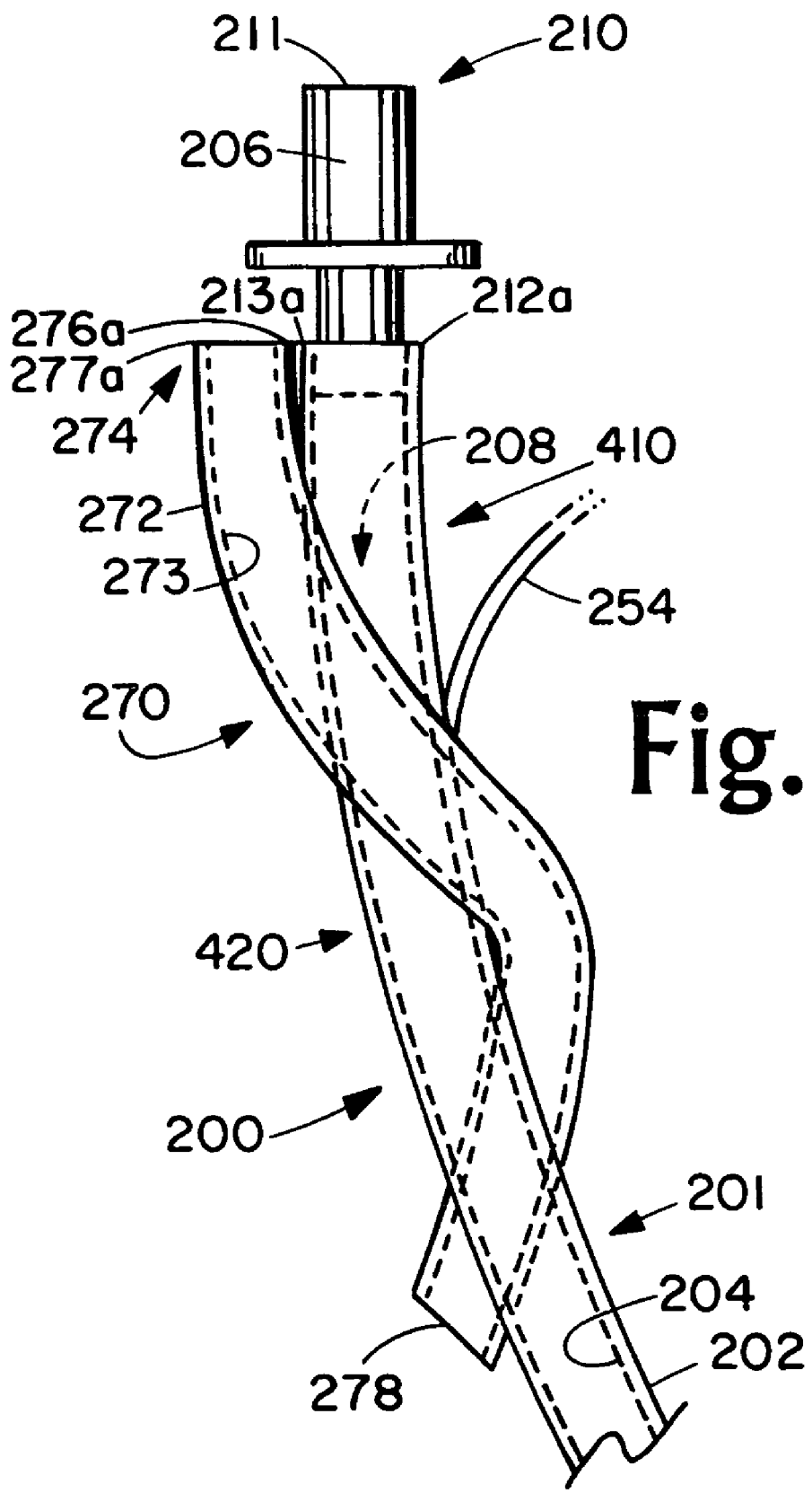

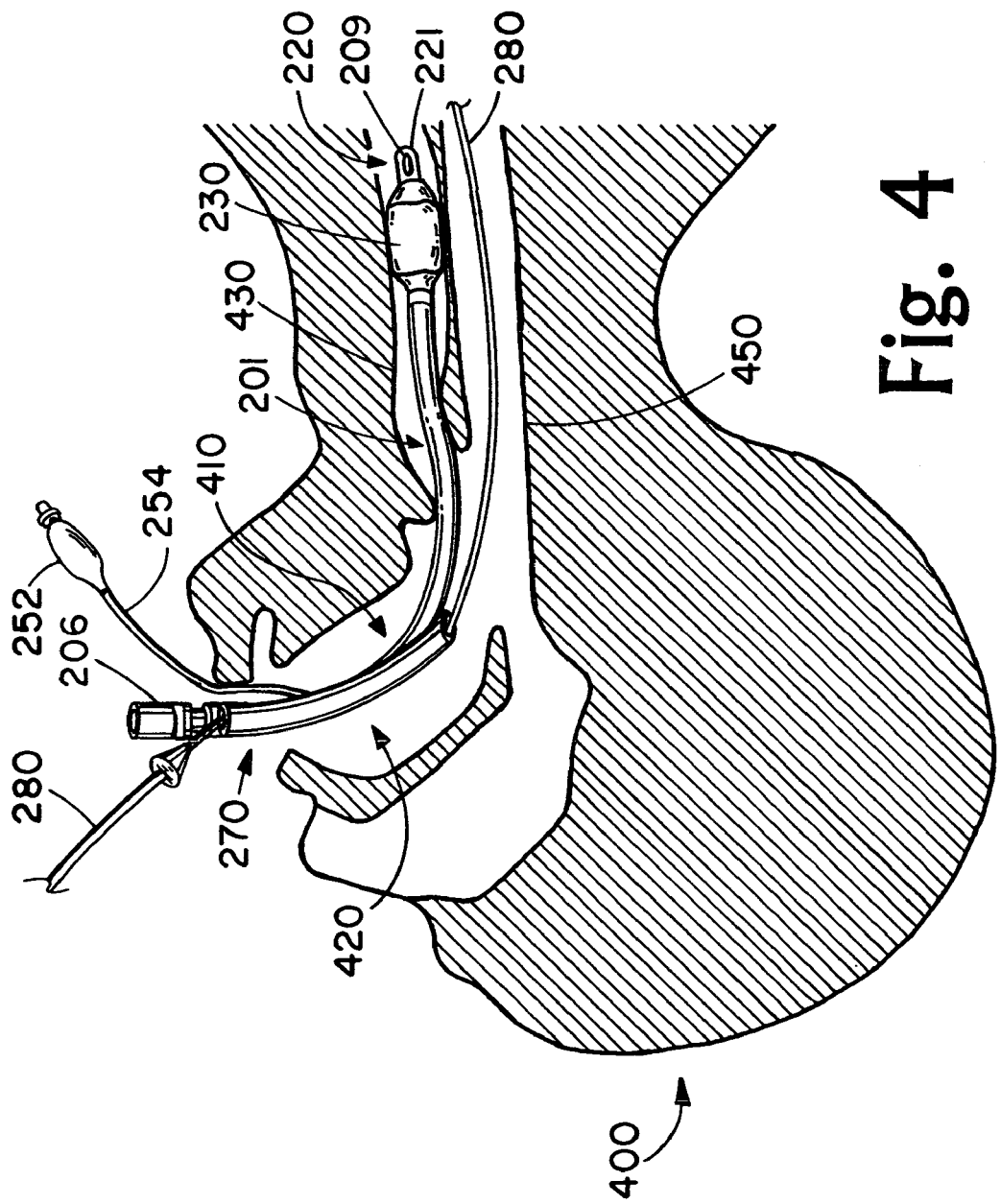

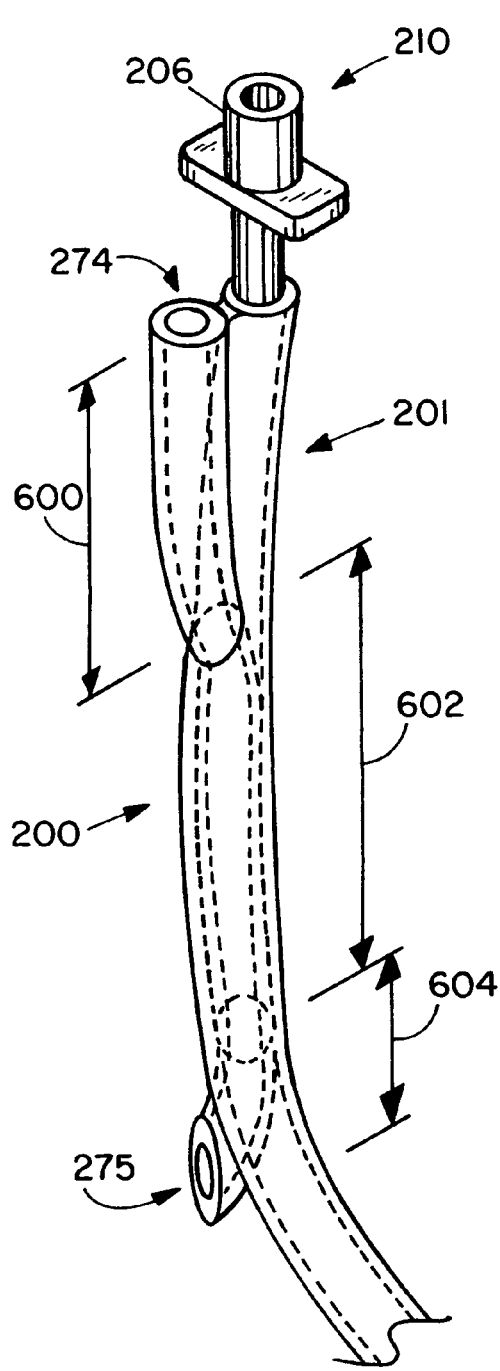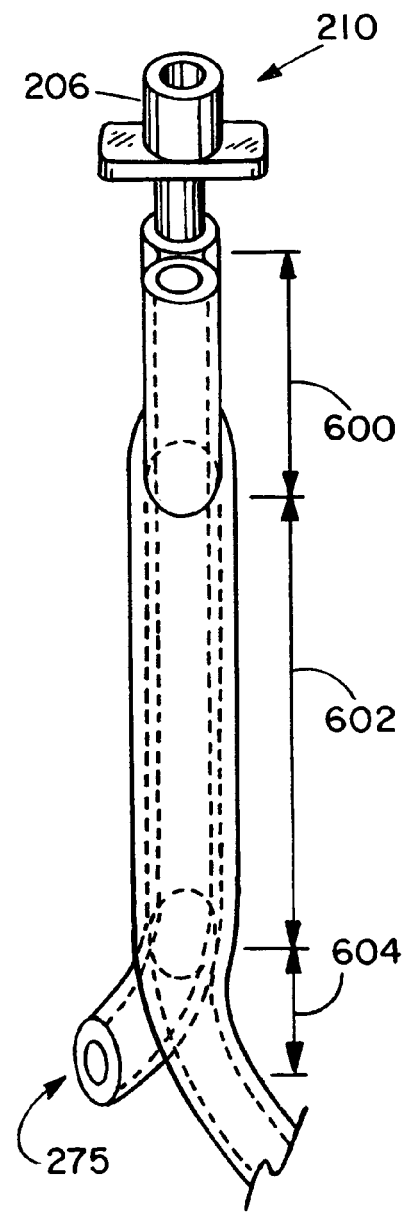
Fig. 6a
Fig. 6b

DEVICE AND METHOD FOR PLACING WITHIN A PATIENT AN ENTERAL TUBE AFTER ENDOTRACHEAL INTUBATION

CROSS-REFERENCE TO RELATED APPLICATIONS

Not applicable.

STATEMENT REGARDING FEDERALLY SPONSORED RESEARCH OR DEVELOPMENT

Not Applicable.

BACKGROUND OF THE INVENTION

The present invention is directed to a novel device and method for providing a disposable endotracheal intubation device for use in conjunction with an auxiliary passageway serving as a guide for the placement of an orogastric or other enterally directed device in a patient.

An early airway apparatus for assisting in artificial respiration of a patient comprised an arcuate, open-ended tubular member which was adapted to be inserted into the patient's trachea. The tubular member carried an external, inflatable resilient sleeve (cuff near the distal end thereof for affecting a seal with the inner wall of the trachea. Following the placement of this endotracheal tube (catheter) respiratory device (a procedure known as endotracheal intubation), it would often be necessary to additionally place within the patient an orogastric (OG) or nasogastric (NG) tube for a number of clinical functions, including, for example, suction of gastric contents, suction of aspiration secretions, suction of air from an inflated stomach, placement of contrast materials and feeding.

However, the placement of an NG tube through the patient's nasal passageway is fraught with potentially serious complications. For example, placement of an NG tube into a patient can cause pressure necrosis of the nasal vestibule, traumatize the nasal mucosa causing massive hemorrhage, puncture the cranial vault, cause toxic shock, perforate the back of the throat, and cause occlusion of facial sinus draining tracts leading to serious infections. Furthermore, passage of an NG tube into a patient many times is only possible by placing one's hand into the patient's posterior orpharynx to facilitate the further directing of the tube into the proximal esophagus.

Similarly, it is often difficult placing an OG tube in a patient due to problems navigating the OG tube past an obstructing tongue of the patient thereby warranting placement of the health practitioner's hand into the patient's posterior orpharynx to direct the tube into the proximal esophagus.

The conventional way of placing the NG and OG tubes after endotracheal intubation place the patient at iatrogenic risk of injury and the health practitioner/operator at risk of being bitten or exposed to enumerable infectious diseases from placing his or her hands into the patient's mouth.

Separate endotracheal, NG and OG tubes are known in the art, as are various devices and methods for using them in combination. A commonly used endotracheal tube utilizes a dual lumen system, where the primary lumen comprises an open-ended tubular member which, when placed into the patient, extends at its distal end into the patient's trachea, and at its opposite end, remains external to the patient. This endotracheal tube commonly employs an external, inflatable resilient sleeve or cuff near the distal end thereof for affecting a seal with the inner wall of the trachea. The sleeve is inflated via a second lumen attached proximate the endotracheal tube.

Dual lumen endotracheal tubes are available under a number of brand names, including the Mallinckrodt® brand. A standard dual lumen endotracheal tube employing an inflatable cuff is shown and described in U.S. Pat. No. 3,625,793 to Sheridan. U.S. Pat. No. 4,584,998 to McGrail (owned by Mallinckrodt), discloses a multi-lumen tracheal tube wherein the standard endotracheal tube employs up to three lumens for conducting various functions associated within the patient's trachea, such as high frequency ventilation. U.S. Pat. No. 5,143,062 to Peckham discloses a standard dual lumen endotracheal tube having a third lumen for use in suctioning the patient's secretions pooled in the trachea above the tube's inflated cuff. Skoljarev—DE19533615 (Abstract) shows an endotracheal tube employing a suction catheter, the tube and catheter encased within an oropharyngeal tube protecting same from being bitten by the patient.

Numerous multi-lumen esophageal/tracheal airway devices exist that are designed to allow for blind (without use of a laryngoscope) insertion of the device into the patient. Typically, these dual lumen airway devices employ one elongated lumen having an inflation cuff similar to a standard endotracheal tube wherein the cuff is located near the distal end of the tube. The other lumen is typically shorter in length and employs an inflation cuff located on the proximal side of openings in the shorter lumen. The device is configured such that either lumen could be used for ventilation regardless of which lumen enters the trachea The non-ventilating lumen can be used to remove gastric fluids. If the longer lumen enters the trachea, its cuff seals the trachea and the longer lumen can be used for ventilation, while the opening of the shorter lumen would be proximate the pharyngeal area of the patient where a seal can be formed to direct gastric fluids into the lumen. This prior art also discloses means of marking the endotracheal tubes with, e.g., an X-ray opaque stripe to facilitate the placement and orientation of the airway and the location of the inflatable cuffs.

For example, Fortuna, US 2004/0020491 A1, describes a combination artificial airway device and esophageal obturator that includes an esophageal cuff and a supraglottic cuff that are inflated in a sequence to provide quick isolation of the esophagus relative to the tracheal air passage. The esophageal cuff is designed to enter the esophagus and to create a seal around the esophagus with the inflatable cuff. The supraglottic cuff does not enter the trachea, but instead inflates to form a seal. Fortuna further describes that if necessary, an orogastric tube can be passed directly to the stomach through the esophageal limb. The portion of the esophageal limb passing through the supraglottic cuff is integrated internal to the supraglottic cuff. A disadvantage of this device is that the airway created is temporary and not secure, and would not be used where medical judgment calls for the use of an endotracheal tube having a cuffed end that physically enters the trachea.

Angel, US 2004/0000314 A1, describes a multi-lumen airway assembly used in a procedure that requires instrumentation to be inserted in an air passage (i.e., larynx, trachea, bronchi or bronchioles) of a patient. The multi-lumen device of Angel is designed to pass through the trachea and into the bronchii. Angel describes an airway assembly employing a reinforced, flexible first conduit, a second conduit (e.g., suction conduit), a third conduit (e.g., ventilation conduit) and an expandable member.

U.S. Pat. No. 5,499,625 to Frass et al. discloses a twin lumen, dual balloon cuff coaxial device designed for use in emergency situations and difficult airways. It can be inserted blindly into the oropharynx and usually enters the esophagus in about 90% of times, and X-ray opaque markings on the lumen assist medical personnel in ascertaining placement and positioning of the device. It is designed to provide effective lung ventilation regardless of whether esophageal or tracheal placement is accomplished. When placed in the trachea, its ventilation function is much like a traditional endotracheal tube. When placed in the esophagus, ventilation is possible through the other coaxial lumen via the use of perforations found between two inflation cuffs.

Ranzinger—US 2003/0183234 A1, describes a dual lumen, dual balloon cuff resuscitation tube. This resuscitation tube comprises a tube wall for alternative artificial endotracheal or esophageal obturator respiration, with a first lumen and a second lumen extending substantially parallel thereto, wherein a first inflatable balloon surrounding the tube wall is disposed in the region of the end of the resuscitation tube facing the body, and a second inflatable balloon surrounding the tube wall is disposed at a separation from the first inflatable balloon, an axial opening of the first lumen is disposed directly at the end of the second balloon facing the body, and the resuscitation tube is formed with one lumen in the region of the first balloon. This permits insertion of intubation aids via the first lumen such that the resuscitation tube can be used with versatility. Similarly with Frass et al., when placed in the trachea, the resuscitation tube's ventilation function is much like a traditional endotracheal tube. When placed in the esophagus, ventilation is possible through the other lumen via the use of perforations found between two inflation cuffs.

Sniadach—US 2003/0062039 A1, describes an intubation system employing an esophageal obturator, and intubation slide, a guide wire and an endotracheal airway tube.

Alfery—U.S. Pat. No. 6,729,325, discloses a perilaryngeal oral airway and supraglottic airway which is capable of acting as an entotracheal tube guide and which seats deep in a patent's hypopharynx to prevent the soft tissue of the glottis and epiglottis from obstructing the airway.

Insler, et al.—U.S. Pat. No. 5,588,424, describes a bronchial blocker endotracheal apparatus employing two lumen. The principal lumen serves to enter and create a cuffed seal within the trachea to ventilate one or both lungs. The second tube also enters the trachea, is permitted to pass below the first lumen's cuff and serves the function of slidably receiving an endobrochial blocker (having a cuffed catheter) that can be positioned into the right or the left bronchus and the cuff inflated to occlude the selected bronchus.

U.S. Pat. Nos. 5,353,787 and 5,253,643, both to Price, disclose an standard endotracheal tube device that is demountably attachable to an oral airway device.

White, et al.—U.S. Pat. No. 4,774,945, discloses a naso-intubation system employing a speech facilitator tube and valve to permit the patient to speak while intubated.

In Scarberry—U.S. Pat. No. 4,351,330, an emergency resuscitation apparatus is provided by an endotracheal tube having a tracheal obturator and a second expandable cuff for sealing against the pharyngeal tissues to provide an alternate sealing means for respiratory fluids if the blind intubation is not successful. Scarberry—U.S. Pat. No. 4,231,365, describes a dual lumen emergency internal defibrillation apparatus.

Dryden—U.S. Pat. No. 4,256,099 and Elam U.S. Pat. No. 4,090,518 also describe a dual lumen resuscitation systems.

Frankel—EPO 0 230 790 discloses an endotracheal tube that is inserted into the patient along a tracked guide located on a flexible tube such as an esophageal tube.

Klepper—U.S. Pat. No. 6,460,540 discloses an endotracheal tube sump assembly attachable to the outside of the endotracheal tube.

Bowden et al.—U.S. Pat. No. 6,374,827 discloses a dual lumen tracheo-esophageal tube and ventilator for pneumatic cardiopulmonary resuscitation.

However, in contrast, none of the above prior art provide an improved device and method to safely facilitate the process of placing within a patient, an enteral tube after endotracheal intubation.

BRIEF SUMMARY OF THE INVENTION

To address the forgoing problems, the present invention teaches a combination intubation device comprising: an endotracheal tube with a substantially circular cross-section, an outside diameter, an inside diameter, a proximal end and a distal end; an inflatable cuff for achieving a seal with an inner wall of the trachea of the patient positioned generally toward the distal end of the endotracheal tube; and a catheter to guide the path of an enteral tube. In a preferred embodiment, the endotracheal tube is capable of defining an arcuate path in a first geometric plane between its proximal end and its distal end to facilitate introduction of the tube into the trachea of a patient. The endotracheal tube has a wall thickness defined as the space between said outside diameter and said inside diameter. The arcuate path, when so defined, has a concave or anterior side and a convex or posterior side substantially opposite the concave side. The endotracheal tube, when so defined in the arcuate path, has a concave or anterior side and a convex or posterior side substantially opposite said concave side.

The inflatable cuff is in fluid communication with an inflation port positioned generally toward the proximal end of the endotracheal tube. The catheter preferably has a substantially circular cross-section, an outside diameter, and an inside diameter suitable to facilitate the smooth movement of the enteral tube therethrough. The enteral tube has an outside diameter of sufficient size to permit its movement through the catheter inside diameter. The catheter has a wall thickness defined as the space between said outside diameter and said inside diameter, and a length defined by a proximal end and a distal end. The catheter preferably has a first side capable of being attached to the endotracheal tube along the length of the catheter. The length of the catheter preferably extends along only a portion of the length of the endotracheal tube. The catheter has a second side substantially opposite said catheter first side. The outside diameter of the endotracheal tube has a first edge along the concave side of the defined arcuate path and a second edge along the convex side of the defined arcuate path. The distal end of the catheter is positioned to facilitate the introduction of the enteral tube into the esophagus of the patient.

The endotracheal tube and catheter can preferably be constructed of a flexible, generally transparent material. In a preferred embodiment, the first side of the catheter is attached to the endotracheal tube along substantially the entire length of the catheter. The catheter is designed to permit entry of any variety of enteral tubes, such as, an orogastric tube. The distal end of the catheter is preferably positioned to direct the path of the enteral tube posteriorly toward the esophagus of the patient. The distal end of the catheter can also be preferably positioned to direct the path of the enteral tube into the gastrointestinal tract of the patient. The distal end of the catheter can be fashioned with a diagonal cut to facilitate the introduction of the enteral tube into the esophagus of the patient.

The positioning of the catheter relative to the endotracheal tube can take on any number of configurations, including, co-axial, helical, semi-helical, integrated, side-by-side, etc. For example, the proximal end of the catheter can be preferably positioned generally within the first plane and the distal end of the catheter positioned generally within the first plane. In another preferred embodiment, the proximal end of the catheter is positioned generally within the first plane and the distal end of the catheter is positioned generally outside of the first plane. In another preferred embodiment, the proximal end of the catheter is positioned generally outside of the first plane and the distal end of the catheter is positioned generally within the first plane. Also, the proximal end of the catheter can be positioned generally outside of the first plane and the distal end of the catheter can be positioned generally outside of the first plane.

In a preferred embodiment, the arcuate path concave or anterior side is generally pointing in a direction away from the patient's vertebra when the endotracheal tube is inserted into the patient, and the arcuate path convex or posterior side is generally pointing toward the patient's vertebra when the endotracheal tube is inserted into the patient. The outside diameter of the endotracheal tube has a first edge along the first side of the arcuate path and a second edge along the second side of the arcuate path. The proximal end of the catheter can be preferably positioned generally within the first plane, the catheter defining a substantially linear path along the second edge of the outside diameter of the endotracheal tube. In another embodiment, the proximal end of the catheter can also be positioned generally outside the first plane, the catheter defining a substantially partial-spiral path around the outside diameter of the endotracheal tube to position the distal end of the catheter in the first plane proximate the second edge of the outside diameter of the endotracheal tube. In a preferred embodiment, the substantially partial spiral path traverses approximately 90-degrees along the outside diameter of the endotracheal tube. In another embodiment, the proximal end of the catheter is side-by-side the endotracheal tube in a second plane substantially normal to the first plane; the distal end of the catheter can be side-by-side the endotracheal tube in a second plane substantially normal to the first plane.

In yet another preferred embodiment, the proximal end of the catheter is positioned generally outside said first plane, the catheter defining a substantially helical path around the outside diameter of said endotracheal tube. In yet another preferred embodiment, the proximal end of the catheter is positioned generally inside said first plane, the catheter defining a substantially helical path around the outside diameter of said endotracheal tube.

In another preferred embodiment of the present invention, the catheter of the present invention further comprises a fenestration along substantially the entire length of the catheter wall to facilitate the removal from the catheter of an enteral tube having previously been placed therethrough without the need to remove the enteral tube from the patient. The fenestration can be located along the outer diameter of the catheter substantially medially between the catheter first side and the catheter second side. In a preferred embodiment, the fenestration is a membrane-like material capable of tearing open sufficient to permit the enteral tube to be pulled substantially laterally through the membrane until the enteral tube is without the catheter. In another preferred embodiment, the fenestration comprises a slit through the entire thickness of the catheter wall thickness along the entire length of the catheter sufficient to permit the enteral tube to be pulled substantially laterally through the slit until the enteral tube is without the catheter. In one embodiment, the slit is maintained in a substantially closed position with a removable strip of tape placed over the slit on the outside diameter of the catheter. The slit preferably has a width of lesser size than the outer diameter of the enteral tube, for example, between ¼ and ½ the size of the outer diameter of the enteral tube.

The catheter can be removably attached to the endotracheal tube. For example, in a preferred embodiment, the catheter further comprises an expandable sleeve connected to the outside diameter of the catheter for attaching the catheter to the endotracheal tube, the expandable sleeve capable of snugly sliding over the outside diameter of the endotracheal tube. The expandable sleeve can further comprise a stretchable material. The sleeve can be connected along a portion of, or substantially the entire length of, the outside diameter of the catheter, and can further comprise one or more expandable sleeves. In another preferred embodiment, the expandable sleeve further comprises one or more closable and reopenable closures connected along the outside diameter of the catheter, the closures being capable of wrapping around the outside diameter of the endotracheal tube to secure the catheter to the endotracheal tube.

In another preferred embodiment, the catheter is fixably attached to the endotracheal tube using any number of methods known in the art, such as, for example and without limitation, extrusion molding, gluing, heat welding, chemical bonding, ring clips, tape, hook and loop fasteners, such as those sold under the VELCRO® brand, mating channels, mated compression fittings, fasteners, clamps and encapsulation with shrink wrap. In one embodiment, the catheter is fixably attached to the endotracheal tube so that a seam is created between the outside diameter of the catheter and the outside diameter of the endotracheal tube, the seam having a length that is adjustable.

In yet another preferred embodiment, the catheter can be removably attached to the endotracheal tube using a variety of methods known in the art. For example, the use of tape, hook and loop fasteners, such as those sold under the VELCRO® brand, mating channels, mated compression fittings, fasteners, clamps and the like can be employed to removably attach the catheter. For example, in a preferred embodiment, the catheter and the endotracheal tube contain mated linear tracks for slidably attaching (or removing) the outer diameter of the catheter to the outer diameter of the endotracheal tube. The catheter can also be slidably attached to the endotracheal tube, where the catheter has one or more cylindrical tubes fixably attached to the anterior side of the catheter, these cylindrical tube(s) being substantially co-axially aligned with each other, and the cylindrical tube(s) having a cross-sectional shape substantially similar to the cross-section of the endotracheal tube, an outside diameter, and an inside diameter suitable to facilitate the frictional movement of the endotracheal tube therethrough, a proximal end and a distal end.

The intubation device of the present invention can also be constructed in a manner that provides unitary construction. For example, the catheter and endotracheal tube can be fully integrated into unitary device. Also, the catheter can comprise a conduit located within the wall of the endotracheal tube.

The intubation device of the present invention can also preferably further comprise: a first section proximate the proximal end of the endotracheal tube wherein the proximal end of the catheter is maintained external to the endotracheal tube, a second section between the proximal and distal ends of the endotracheal tube wherein the catheter is maintained within the endotracheal tube, and a third section toward the distal end of the endotracheal tube wherein the distal end of the catheter is maintained external to the endotracheal tube. In another preferred embodiment, the intubation device of the present invention further comprises: a first section proximate the proximal end of the endotracheal tube wherein the proximal end of the catheter is maintained within the wall of the endotracheal tube, the proximal end of the catheter being flush with the outside diameter of the endotracheal tube and remaining capable of having the enteral tube pass therethrough; a second section between the proximal and distal ends of the endotracheal tube wherein the catheter is maintained within the endotracheal tube; and a third section toward the distal end of the endotracheal tube wherein the distal end of the catheter is maintained within the wall of the endotracheal tube, the distal end of the catheter being flush with the outside diameter of the endotracheal tube and remaining capable of having the enteral tube pass therethrough.

In another preferred embodiment, the intubation device of the present invention preferably further comprises an endotracheal tube axis located in the distal portion of the endotracheal tube, the endotracheal tube axis being substantially aligned with the axis of the patient's trachea when the distal end of the endotracheal tube is placed within the patient's trachea; a first catheter zone located between the proximal and distal ends of the catheter, wherein the catheter has a first catheter axis that is substantially parallel to the endotracheal tube axis; and a second catheter zone located proximate the distal end of the catheter wherein the catheter has a second catheter axis that diverges from the first catheter axis. In a preferred embodiment, the second catheter axis diverges from the first catheter axis to direct the path of the enteral tube posteriorly toward the esophagus of the patient. In another preferred embodiment, the second catheter axis diverges from the first catheter axis to form an angle between both axes to optimally align the distal end of the catheter for directing the path of the enteral tube posteriorly toward the esophagus of the patient. The angle can preferably be between about 15 degrees and 60 degrees.

In another preferred embodiment of the present invention, the intubation device further comprises a malleable stylet for use in shaping the device. In one example, the endotracheal tube (and/or the catheter) further comprises a malleable stylet for use in shaping the endotracheal tube (and/or the catheter), the stylet having a distal end and a proximal end. The stylet can employ fiber optics capable of transmitting an optical image signal from the distal end of the stylet to a display device connected to the proximal end of the stylet. In a preferred embodiment, the stylet is integrated into the endotracheal tube (and/or catheter), such as by being built into the wall of the endotracheal tube (and/or catheter). Alternatively, the stylet is insertable into and removable from the inside diameter of the endotracheal tube and/or catheter.

In another preferred embodiment, the endotracheal tube (and/or catheter) further comprises one or more strands of a flexible, memory retaining material capable of being manipulated to facilitate the defining of the arcuate path or otherwise to facilitate the shaping of the endotracheal tube and/or catheter. Additionally, the endotracheal tube of the present invention may contain a manual curvature adjustment ring to likewise facilitate the defining of the arcuate path or otherwise to facilitate the shaping of the endotracheal tube.

In another preferred embodiment of the present invention, there is disclosed a combination medical device comprising: an endotracheal tube with a substantially circular cross-section, an outside diameter, an inside diameter, a proximal end and a distal end; and a catheter to guide the path of an enteral tube. The endotracheal tube defines an arcuate path in a first plane between its proximal end and its distal end to facilitate introduction of the tube into the trachea of a patient. The endotracheal tube employs an inflatable cuff for achieving a seal with an inner wall of the trachea of the patient positioned generally toward the distal end of the endotracheal tube, the inflatable cuff being in fluid communication with an inflation port positioned generally toward the proximal end of the endotracheal tube. The catheter has a substantially circular cross-section, an outside diameter, and an inner diameter suitable to facilitate the smooth movement of the enteral tube therethrough, and a length defined by a proximal end and a distal end. The catheter is attached to the endotracheal tube along substantially the entire length of said catheter, the proximal end of the catheter being positioned generally outside the first plane, the length of the catheter extending along only a portion of the length of the endotracheal tube. In this embodiment, the catheter defines a substantially partial-spiral path around the outside diameter of the endotracheal tube to position the distal end of the catheter in the first plane, the distal end of the catheter having a diagonal cut at the end to facilitate the introduction of the enteral tube into the esophagus of the patient. The catheter of this embodiment can also comprise a fenestration along substantially the entire length of the catheter wall to facilitate the removal from the catheter of an enteral tube having previously been placed therethrough without the need to remove the enteral tube from the patient.

The endotracheal tube of the present invention can also employ markings to assist medical personnel in ascertaining placement and positioning of the device.

In yet another preferred embodiment of the present invention, there is disclosed an endotracheal intubation device comprising:

a substantially circular cross-section, an outside diameter, an inside diameter, a proximal end, a distal end, a wall thickness defined as the space between the outside diameter and the inside diameter;

the endotracheal intubation device capable of defining an arcuate path in a first geometric plane between its proximal end and its distal end to facilitate introduction of the tube into the trachea of a patient, the arcuate path, when so defined, having a concave side and a convex side substantially opposite said concave side, the endotracheal tube, when so defined in the arcuate path, having a concave side and a convex side substantially opposite said concave side, a malleable stylet for use in shaping said endotracheal intubation device;

the stylet having a distal end and a proximal end and being integrated into said wall thickness; and an inflatable cuff for achieving a seal with an inner wall of the trachea of the patient positioned generally toward the distal end of said endotracheal intubation device, the inflatable cuff being in fluid communication with an inflation port positioned generally toward the proximal end of said endotracheal tube.

In this embodiment, the stylet can further comprise one or more strands of a flexible, memory retaining material capable of being manipulated to facilitate the defining of the arcuate path. Additionally, if desired, this intubation device can employ integrated fiber optics capable of transmitting an optical image signal from the distal end to a display device.

In yet another preferred embodiment of the present invention, there is described a method of intubating a patient comprising the steps of: (a) providing an intubation device in accordance with embodiments of the present invention; (b) inserting into the oral cavity of a patient the intubation device oriented such that the distal end of the endotracheal tube enters first, (c) orienting the distal end of the endotracheal tube with the patient's trachea; (d) inserting the distal end of the endotracheal tube into the patient's trachea; (e) inflating the inflatable cuff by administering a source of air into the inflation port; and ventilating the patient through the endotracheal tube. A preferred embodiment includes the additional step of directing a desired enteral tube into the proximal end of the catheter, through the catheter, out the distal end of the catheter and into the desired location of the patient. Another preferred embodiment of this method includes the additional step of removing the intubation device without removing said enteral tube from said desired location within the patient.

When the catheter of the intubation device of the present invention includes the fenestration feature, a preferred embodiment of the present inventive method can also include the additional steps of: deflating the inflatable cuff of the endotracheal tube; maintaining the enteral tube in its desired location while withdrawing the intubation device from the patient's oral cavity; and maintaining the enteral tube in its desired location while directing the enteral tube through the fenestration.

When the catheter of the intubation device of the present invention includes an integrated, malleable stylet for use in shaping the intubation device, a preferred embodiment of the present inventive method can also include the additional step of: shaping the intubation device prior to inserting the device into the oral cavity of a patient so that the shape of the intubation device facilitates the insertion of the device into the oral cavity of the patient.

When the catheter of the intubation device of the present invention includes an integrated array of fiber optics capable of transmitting an optical image signal from the distal end of the device to a display device external to the patient, a preferred embodiment of the present inventive method can also include the additional step of: viewing the display of the fiber optics image signal on the display device while inserting the intubation device into the patient to facilitate placement of the intubation device.

BRIEF DESCRIPTION OF THE SEVERAL VIEWS OF THE DRAWINGS

FIG. 2b illustrates a substantially right side perspective view of the intubation device of FIG. 2a (rotated partially counterclockwise about the longitudinal axis of the device) according to a preferred embodiment of the present invention.

FIG. 2c illustrates a substantially underside (posterior) perspective view of the intubation device of FIG. 2a (rotated ninety degrees counterclockwise about the longitudinal axis of the device shown in FIG. 2b) according to a preferred embodiment of the present invention.

FIG. 2d illustrates a substantially left side perspective view of the intubation device of FIG. 2a (rotated ninety degrees counterclockwise about the longitudinal axis of the device shown in FIG. 2c) according to a preferred embodiment of the present invention.

FIG. 2g illustrates a side view of an intubation device using a helical catheter configuration according to a preferred embodiment of the present invention.

FIG. 2h illustrates a geometric (coronal) plane view of the intubation device taken along the coronal cutting plane line 2h-2h of FIG. 2a.

FIG. 2i illustrates a geometric (saggital) plane view taken along the saggital cutting plane line 2i-2i of FIG. 2a.

FIG. 3a is a cross sectional view of one preferred embodiment of the present invention taken across line 3a-h-3a-h of FIG. 2a.

FIG. 3b is a cross sectional view of one preferred embodiment of the present invention taken across line 3a-h-3a-h of FIG. 2a.

FIG. 3c is a cross sectional view of one preferred embodiment of the present invention taken across line 3a-h-3a-h of FIG. 2a.

FIG. 3d is a cross sectional view of one preferred embodiment of the present invention taken across line 3a-h-3a-h of FIG. 2a.

FIG. 3e is a cross sectional view of one preferred embodiment of the present invention taken across line 3a-h-3a-h of FIG. 2a.

FIG. 3f a cross sectional view of is one preferred embodiment of the present invention taken across line 3a-h-3a-h of FIG. 2a.

FIG. 3g is a cross sectional view of one preferred embodiment of the present invention taken across line 3a-h-3a-h of FIG. 2a.

FIG. 3h is a cross sectional view of one preferred embodiment of the present invention taken across line 3a-h-3a-h of FIG. 2a.

FIG. 4 is a side elevational, saggital view of a patient with an endotracheal intubation employing one preferred embodiment of the present intubation invention shown in perspective view.

FIG. 6a illustrates a perspective top side (anterior) view of an intubation device according to another preferred embodiment of the present invention.

FIG. 6b illustrates a substantially right side perspective view of the intubation device of FIG. 6a (rotated partially counterclockwise about the longitudinal axis of the device) according to a preferred embodiment of the present invention.

DETAILED DESCRIPTION OF THE INVENTION

Figure 1:
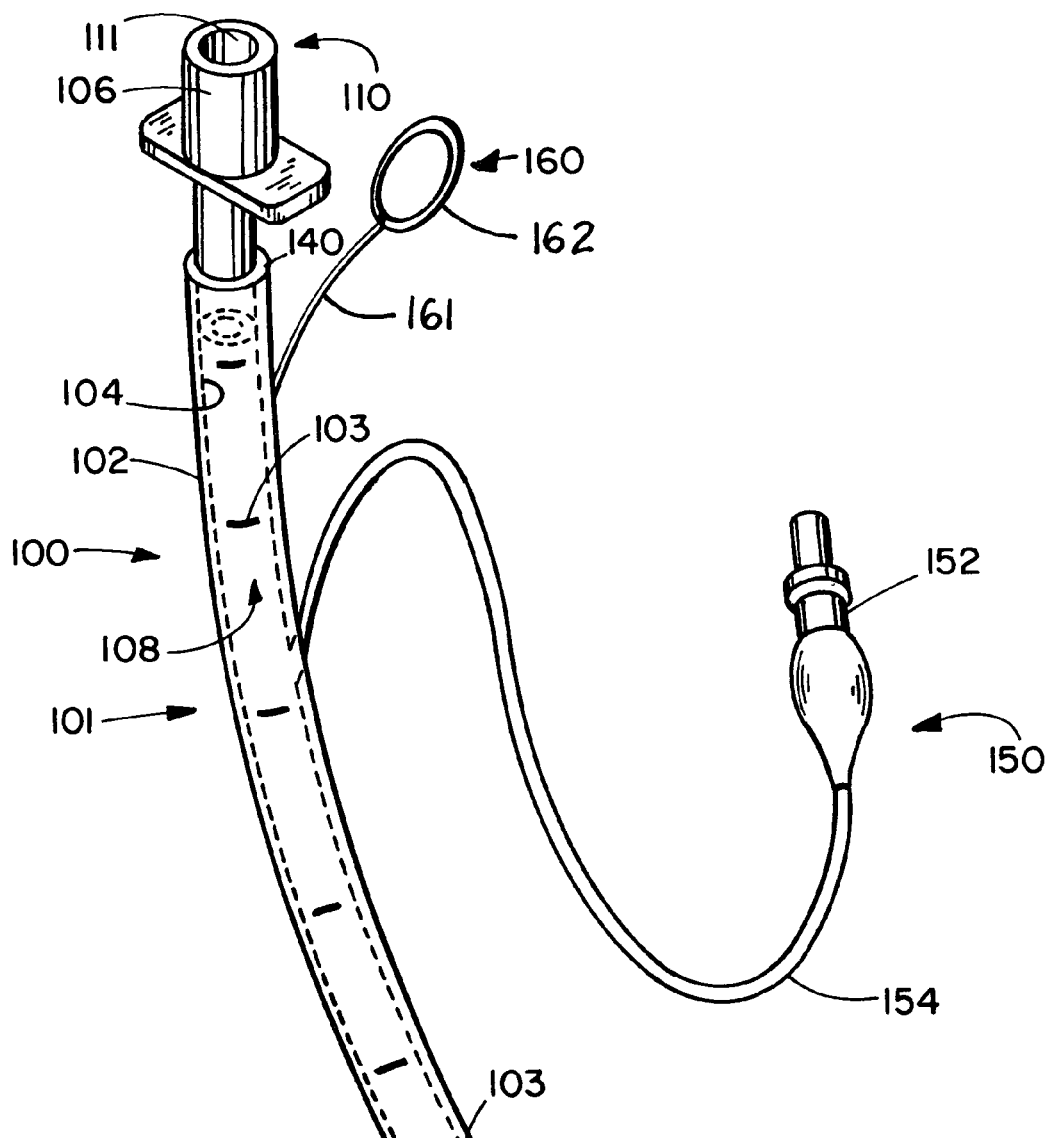
FIG. 1 shows a perspective view of a prior art endotracheal tube.

Referring now to FIG. 1, there is shown a representative endotracheal tube 100 known in the prior art having a lumen 101 having a substantially circular cross-section, an outside wall 102 having an outside wall diameter, an inside wall 104 having an inside wall diameter, a proximal end 110 and a distal end 120. The endotracheal tube 100 employs at its proximal end 110 a connector device 106 for connecting to a means of ventilation (not shown) such as ventilation source, bag valve and the like for providing a source of air to the patient's lungs through the internal conduit 108 within the lumen 101 of the endotracheal tube 100. The tube 100 has a proximal opening 111. At the distal end 120 of the endotracheal tube 100 the tube is typically bevel-shaped to facilitate introduction into the patient's trachea. Also shown in the distal region of the tube 100 is the distal opening 121 and a "Murphy's eye" suction opening 109 for suctioning fluids from below the cuff. The proximal opening 111 and the distal opening 121 are in fluid communication with each other. An inflatable balloon cuff 130 for achieving a seal with an inner wall of the trachea of the patient is positioned generally toward the distal end 120 of the endotracheal tube 100. The endotracheal tube lumen 101 has a wall thickness 140 defined as the space between the outside diameter 102 and the inside diameter 104. The inflatable cuff 130 is in fluid communication with an inflation port assembly 150 positioned generally toward the proximal end 110 of the endotracheal tube 100.

The inflation port assembly 150 comprises a pilot balloon and valve 152 for use in providing air to or releasing air from the inflatable cuff 130 via cuff inflation tube 154 and its opening 156 into the cuff interior 131. The pilot balloon and valve 152 are in fluid communication with the inflation tube 154 and the cuff interior 131. The cuff 130 is attached to the exterior of the lumen 101 in sealed fashion so that when air enters the interior space 131 of the cuff 130 through opening 156, the cuff will inflate until it is in sealed contact with the patient's tracheal walls. The endotracheal tube 100 can also include a manual curvature adjustment ring device 160 such as used in the Mallinckrodt® brand "endotrol tube". This ring structure 160 includes a wire 161 attached to a pull ring 162, wherein the wire 161 is, e.g., embedded within the wall 140 of the endotracheal tube 100 such that pulling on the ring 162 will cause the tube 100 to bend in a manner that facilitates insertion of the tube lumen 101 into the patient's trachea. The lumen 101 can be marked with visible and/or X-ray opaque (or radiopaque) stripes or markings 103 (generally shown), or other suitable means to facilitate the placement and orientation of the airway 100 and the location of the inflatable cuff 130 within the patient.

Referring now to FIGS. 2a-2g, there are shown novel dual lumen intubation devices 200 having an endotracheal lumen 201 with substantially circular cross-section, an outside wall 202 having an outside wall diameter, an inside wall 204 having an inside wall diameter, a proximal end 210 and a distal end 220. The endotracheal lumen component 201 of the intubation device 200 employs at its proximal end 210 a connector device 206 for connecting to a means of ventilation (not shown) such as ventilation source, ambu bag, bag valve and the like for providing a source of air to the patient's lungs through the internal conduit 208 within the endotracheal lumen 201 of the intubation device tube 200. The endotracheal lumen 201 has a proximal opening 211. At the distal end 220 of the endotracheal lumen 201 the lumen is typically bevel-shaped to facilitate introduction into the patient's trachea. Also shown in the distal region of the endotracheal lumen 201 is the distal opening 221 and a "Murphy's eye" suction opening 209 for suctioning fluids from below the cuff 230.

The proximal opening 211 and the distal opening 221 are in fluid communication with each other. An inflatable balloon cuff 2 for achieving a seal with an inner wall of the trachea of the patient (not shown) is positioned generally toward the distal end 220 of the endotracheal lumen 201. The endotracheal lumen 201 has a wall thickness 240 defined as the space between the outside diameter 202 and the inside diameter 204. The inflatable cuff 230 is in fluid communication with an inflation port assembly 250 positioned generally toward the proximal end 210 of the endotracheal lumen 201. The inflation port assembly 250 comprises, for example, a pilot balloon and valve 252 for use in providing air to or releasing air from the inflatable cuff 230 via cuff inflation tube 254 and its opening 256 into the interior space 231 of the cuff 230. The pilot balloon and valve 252 are in fluid communication with the inflation tube 254 and the cuff interior 231. The cuff 230 is attached to the exterior of the endotracheal lumen 201 in sealed fashion so that when air enters the interior space 231 of the cuff 230 through opening 256, the cuff will inflate until it is in sealed contact with the walls of the patient's trachea. The endotracheal lumen 201 can also include a manual curvature adjustment ring (not shown) such as used in the Mallinckrodt® brand "endotral tube" (see element 160 of FIG. 1 and associated text).

FIG. 4 is a side cross sectional (saggital) view of a patient with an endotracheal intubation employing one preferred embodiment of the present intubation invention. Referring to FIG. 4, in conjunction with FIGS. 2a-2i, the endotracheal lumen 201 is capable of defining an arcuate path in a first geometric plane (or saggital plane) between its proximal end 210 and its distal end 220 to facilitate introduction of the endotracheal lumen 201 into the trachea 430 of a patient. The first geometric or saggital plane is depicted in FIG. 2i as the saggital cutting plane line of the lumen 201 taken from line 2i-2i of FIG. 2a. The arcuate path, when so defined, has a concave or anterior side 410 and a convex or posterior side 420 substantially opposite the concave side. The endotracheal lumen 201, when so defined in the arcuate path, has a concave or anterior side 410 and a convex or side 420 substantially opposite the concave side. Referring to FIG. 2h, there is shown a second geometric plane (or coronal plane) taken along the coronal cutting plane of the lumen 201 (line 2h-2h of FIG. 2a).

Attached (permanently, semipermanently, or removably) to the endotracheal lumen 201 is catheter 270 to guide the path of an enteral tube 280, such as the Bard® Nasogastric Sump Tube, into the esophagus 450 of the patient 400. The enteral tube 280 can be marked with visible and/or X-ray opaque (or radiopaque) stripes or markings (not shown), or other suitable means to facilitate the placement and orientation of the enteral tube 280 within the patient. The enteral tube 280 can employ as an option a locking device 281 to hold the enteral tube 280 in place relative to the catheter 270. The catheter 270 preferably has a substantially circular cross-section, an outside wall 272 defining an outside diameter, and an inside wall 273 defining an inside diameter suitable to facilitate the smooth movement of the enteral tube 280 therethrough.

The enteral tube 280 has an outside diameter of sufficient size to permit its movement through the catheter inside diameter 271. The catheter 270 has a wall thickness defined as the space between the outside diameter 272 and the inside diameter 273, and a length defined by a proximal end 274 and a distal end 275. The catheter 270 preferably has a first side 276 capable of being attached to the endotracheal lumen 201 along the length of the catheter 270. The length of the catheter 270 preferably extends along only a portion of the length of the endotracheal lumen 201. The catheter 270 has a second side 277 substantially opposite the catheter first side 276. The outside diameter of the endotracheal lumen 201 has a first edge 212 and a second edge 213. The distal end 275 of the catheter 270 is positioned to facilitate the introduction of the enteral tube 280 into the esophagus of the patient.

The endotracheal lumen 201 and/or the catheter 270 can be marked with visible and/or X-ray opaque (or radiopaque) stripes or markings 203 (generally shown), or other suitable means to facilitate the placement and orientation of the intubation device 200 and the location of the inflatable cuff 230 within the patient.

The endotracheal lumen 201 and catheter 270 can preferably be constructed of a flexible, generally transparent material. In a preferred embodiment, the first side 276 of the catheter 270 is attached to the endotracheal lumen 201 tube along substantially the entire length of the catheter 270. The catheter 270 is designed to permit entry of any variety of enteral tubes 280, such as, an orogastric tube. The distal end 275 of the catheter 270 is preferably positioned to direct the path of the enteral tube 280 posteriorly toward the esophagus 450 of the patient 400. The distal end 275 of the catheter 270 can also be preferably positioned to direct the path of the enteral tube 280 into the gastrointestinal tract of the patient (not shown). The distal end 275 of the catheter 270 can be fashioned with a diagonal cut 278 to facilitate the introduction of the enteral tube 280 into the esophagus of the patient.

The positioning of the catheter 270 relative to the endotracheal lumen 201 can take on any number of configurations, including, co-axial, helical, semi-helical, integrated, side-by-side, etc.

For example, in a preferred embodiment of the present invention, the proximal end of the catheter 274 is positioned generally outside of the first or saggital plane in the second or coronal plane and the distal end of the catheter 275 is positioned generally within the first or saggital plane such as depicted generally in FIGS. 2a-2d.

Figure 2A:
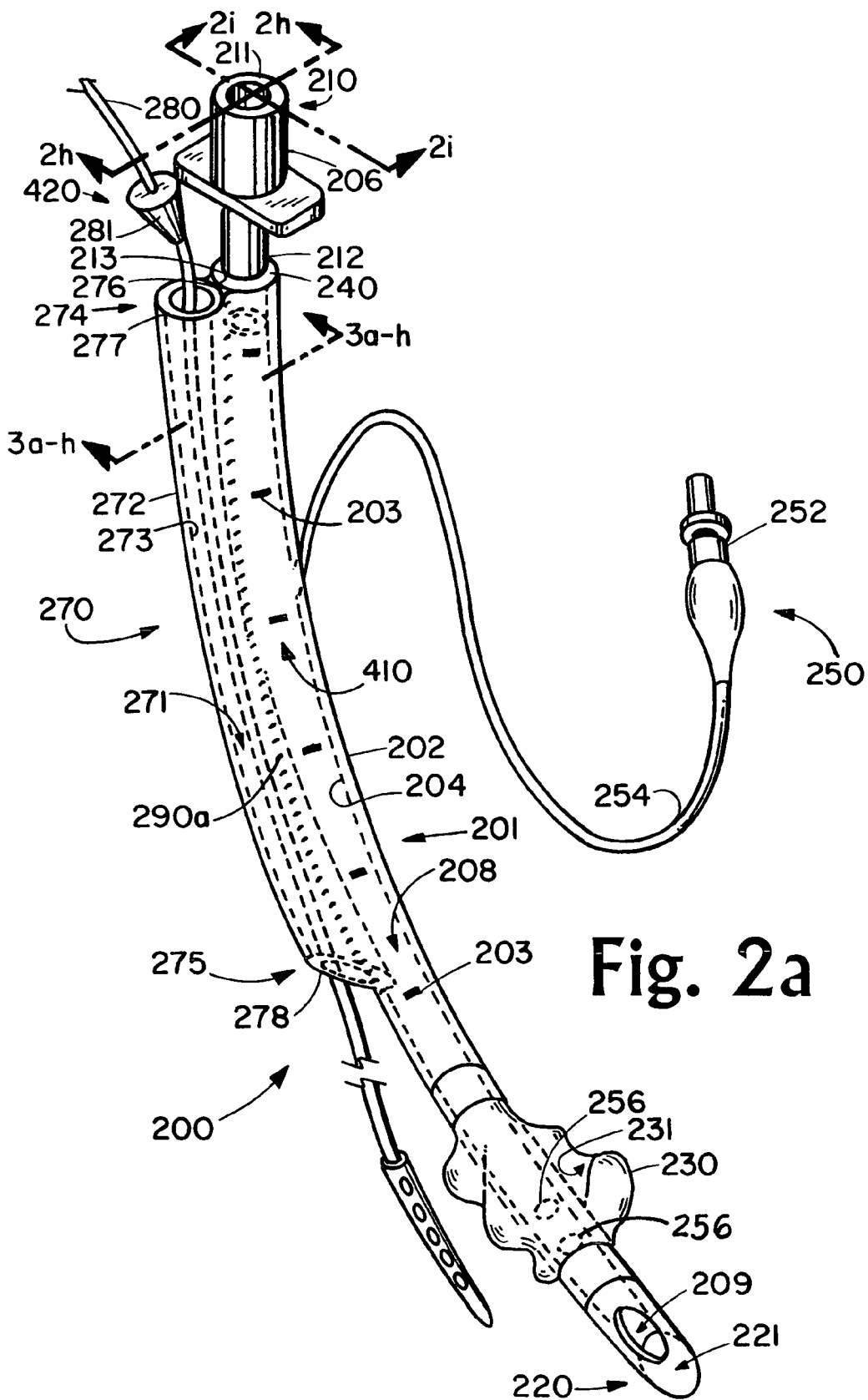
FIG. 2a illustrates a perspective top side (anterior) view of an intubation device according to a preferred embodiment of the present invention.
Figure 2E:
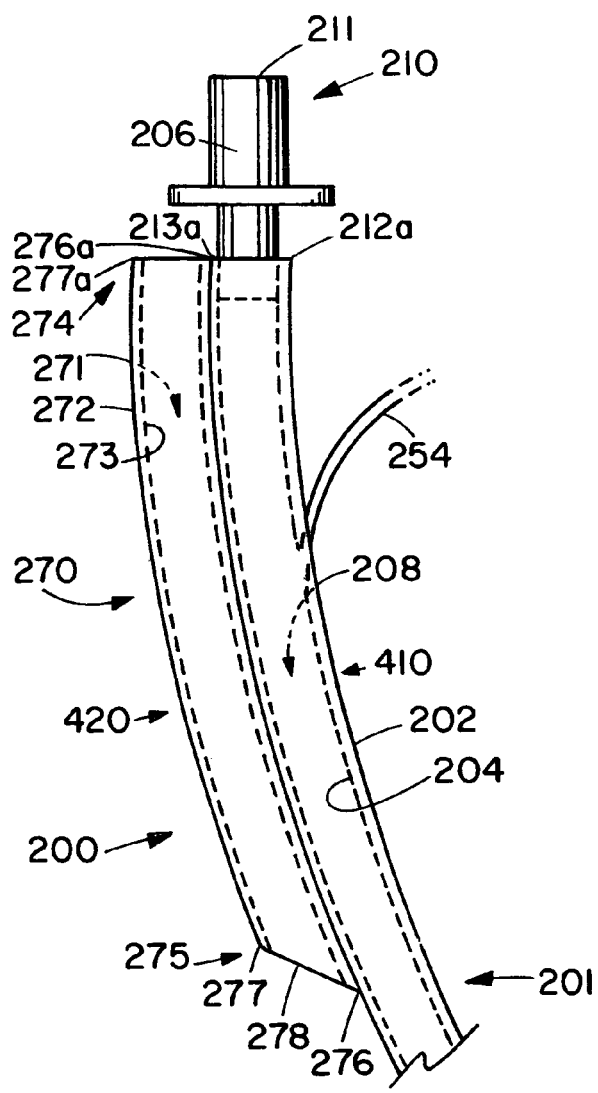
FIG. 2e illustrates a side view of an intubation device using a top-to-bottom catheter configuration according to a preferred embodiment of the present invention.

Referring to FIG. 2e, in another preferred embodiment, the proximal end of the catheter 274 can be preferably positioned generally within the first or saggital plane of the lumen 201 and the distal end of the catheter 275 also positioned generally within the first or saggital plane, such that both the catheter 274 and the lumen 201 are substantially top-to-bottom, lying within the same sattigal plane.

In another preferred embodiment, the proximal end of the catheter 274 is positioned generally within the first or saggital plane of the lumen 201 and the distal end of the catheter 275 is positioned generally outside of the first or saggital plane in the second or coronal plane of the lumen 201, such as depicted in FIG. 2g.

Also, the proximal end of the catheter 274 can be positioned generally outside of the first or saggital plane in the second or coronal plane and the distal end of the catheter 275 can be positioned generally outside of the first or saggital plane in the second or coronal plane such as depicted in FIGS. 2e and 2g. The catheter 270 preferably has a first side 276a capable of being attached to the endotracheal lumen 201 along the length of the catheter 270. The length of the catheter 270 preferably extends along only a portion of the length of the endotracheal lumen 201. The catheter 270 has a second side 277a substantially opposite the catheter first side 276a The outside diameter of the endotracheal lumen 201 has a first edge 212a along the concave side of the defined arcuate path and a second edge 213a along the convex side of the defined arcuate path.

Furthermore, the catheter 270 could have a helical configuration relative to the endotracheal lumen 201 such as shown, for example, in FIG. 2g.

Referring to FIGS. 3a-3h, there are depicted some examples of the possible attachment relationships between the catheter 270 and the lumen 201. For example, the catheter and lumen can be attached by a zone of attachment or seam 290a, 290b, 290d, 290e, 290f, 290g that can be created by, e.g., heat welding, gluing, molding, or other means of attachment. The seam can be permanent, or can be designed to be temporary or adjustable in length. For example, the seam 290 could comprise a width of webbed material that could be cut or torn without destroying the integrity of interior spaces 271 and 208 of the catheter and lumen, respectively. A mated channel assembly 291, 292 (FIG. 3g) could also be employed to attach the catheter to the lumen. Additionally, the catheter and lumen could be attached using a clip assembly 293 comprising one or more C-shaped fingers 294, 295 that could snap over the outer diameter of the catheter and lumen (FIG. 3c), and if desired, the clip assembly 293 could be an integral part of lumen 201. Additionally, the cross-sectional profile of the intubation device could be substantially oval in shape as depicted in FIGS. 3b and 3d-f.

Referring again to FIG. 4 in conjunction with FIGS. 2a-2i, in a preferred embodiment, the arcuate path concave or anterior side 410 is generally pointing in a direction away from the patient's vertebra (not shown) when the intubation device 200 is inserted into the patient 400, and the arcuate path convex or posterior side 420 is generally pointing toward the patient's vertebra (not shown) when the intubation device 200 is inserted into the patient 400. The outside diameter 202 of the endotracheal lumen 201 has a first edge 212 along the first side of the arcuate path and a second edge 213 along the second side of the arcuate path. In one preferred embodiment, the proximal end of the catheter 274 can be preferably positioned generally within the first or saggital plane (one under the other) with the endotracheal tube 201), the catheter defining a substantially linear path along the second edge 213 of the outside diameter of the endotracheal tube 201 (e.g., FIG. 2e, 213a, 212a).

In another embodiment, the proximal end 274 of the catheter 270 can be positioned generally outside the first or saggital plane in the second or coronal plane (side-by-side with the endotracheal tube 201) (e.g., FIGS. 2a-2d), the catheter 270 defining a substantially partial-spiral path around the outside diameter 202 of the endotracheal tube 201 to position the distal end 275 of the catheter 270 in the first or saggital plane proximate the second edge 213 of the outside diameter 202 of the endotracheal tube 201. In a preferred embodiment, the substantially partial spiral path traverses approximately 90-degrees along the outside diameter of the endotracheal tube.

Figure 2F:
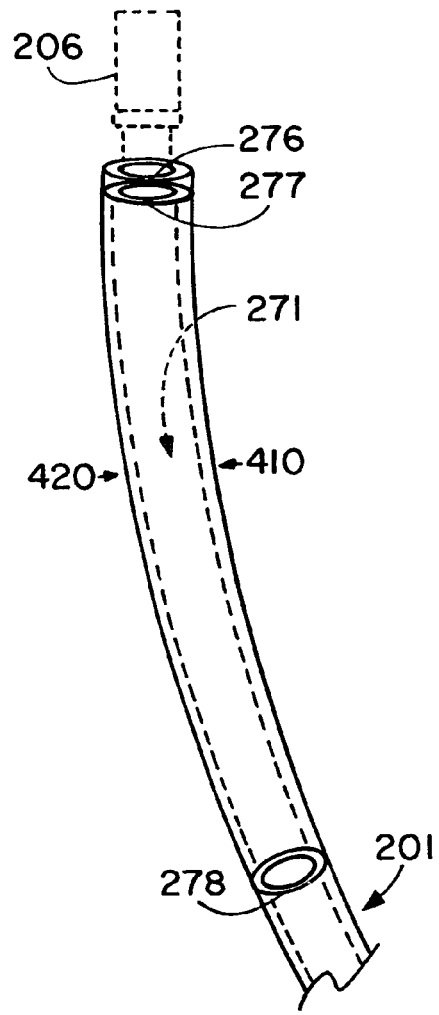
FIG. 2f illustrates a side view of an intubation device using a side-by-side catheter configuration according to a preferred embodiment of the present invention.
Figure 2H:
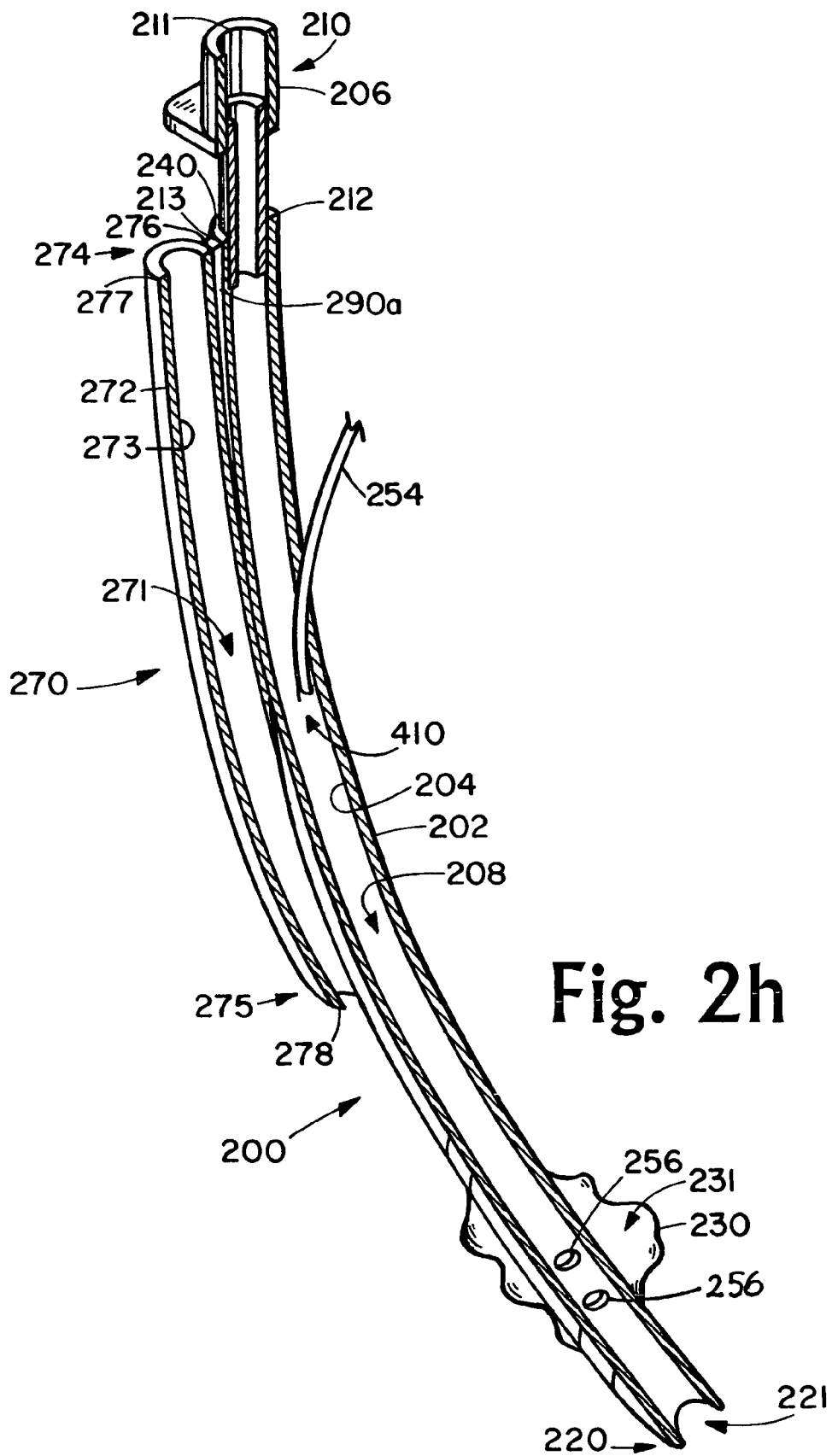
Figure 2I:
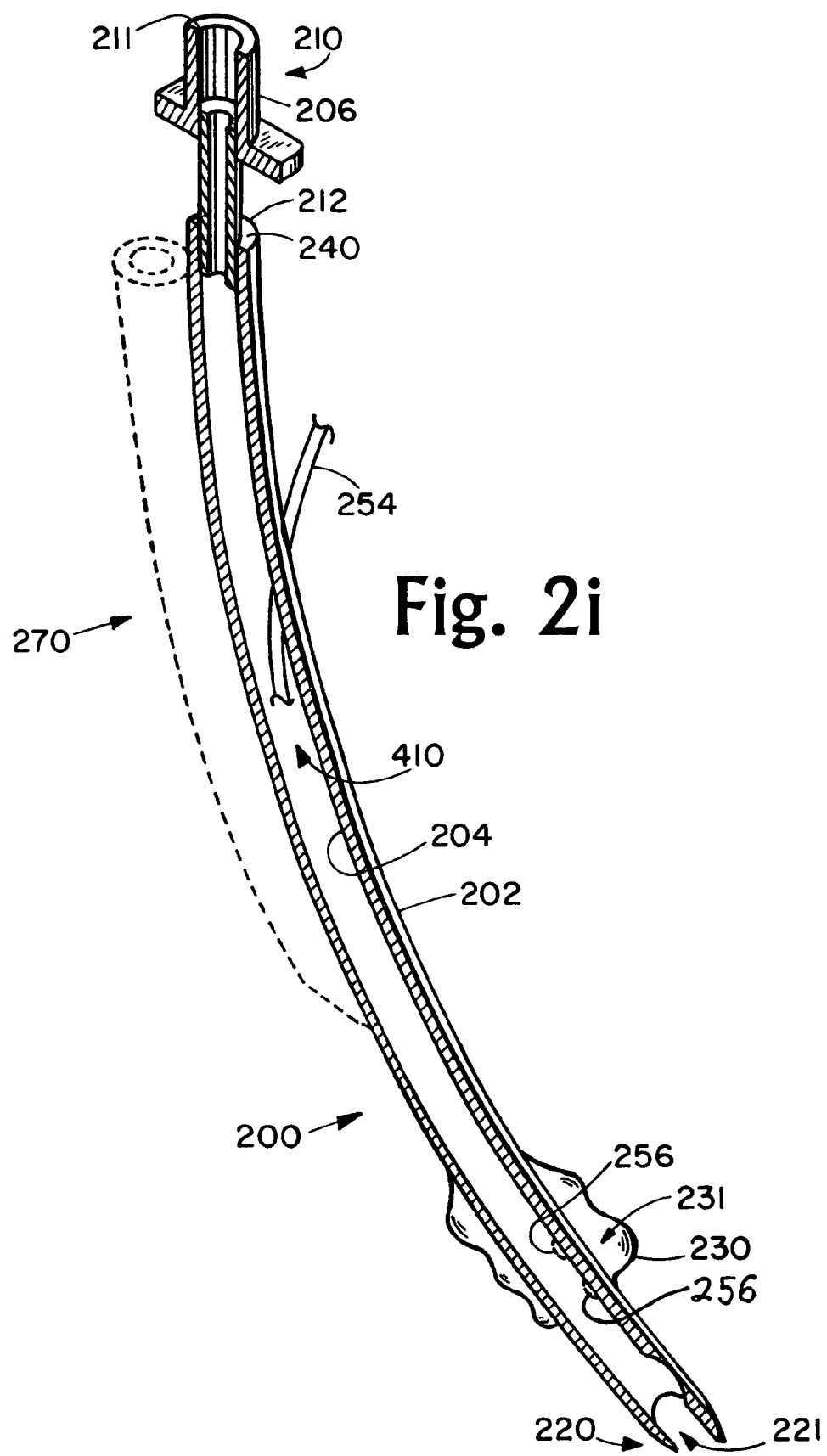

In another embodiment, the proximal end 274 of the catheter 270 is side-by-side the endotracheal tube 201 in a second plane substantially normal to the first plane; the distal end 275 of the catheter 270 can be side-by-side the endotracheal tube in the second plane substantially normal to the first plane (e.g., FIG. 2f).

In yet another preferred embodiment, the proximal end 274 of the catheter 270 is positioned generally outside the first plane, the catheter defining a substantially helical path around the outside diameter of the endotracheal tube 201.

In yet another preferred embodiment, the proximal end 274 of the catheter 270 is positioned generally inside the first plane, the catheter 270 defining a substantially helical path around the outside diameter 202 of the endotracheal tube 201 (e.g., FIG. 2g).

Figure 3A:
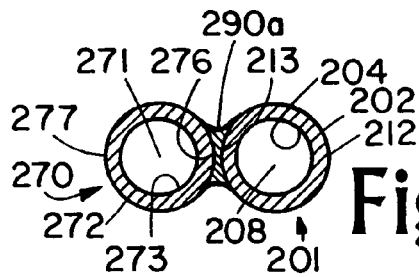
Figure 3B:
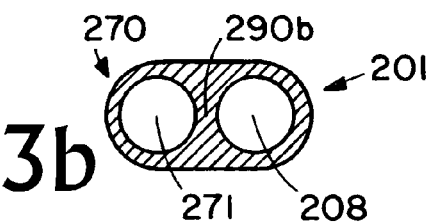
Figure 3C:
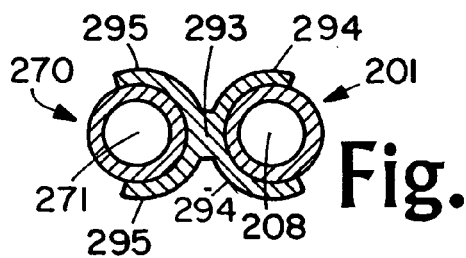
Figure 3D:
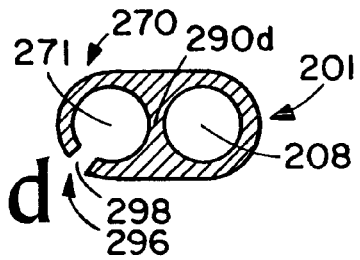
Figure 3E:
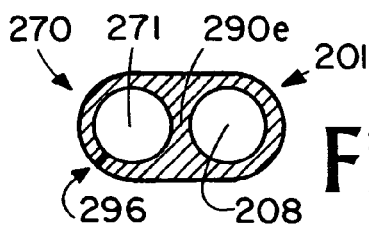
Figure 3F:
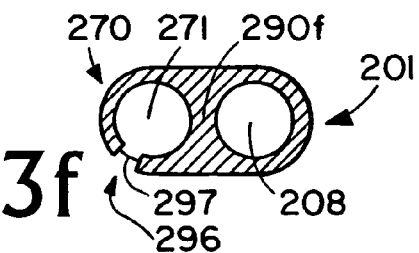
Figure 3G:
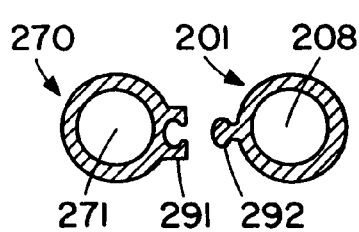
Figure 3H:
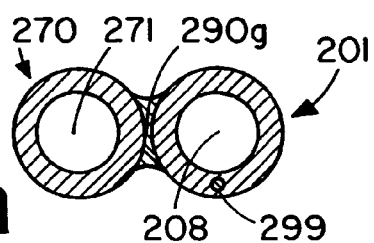

Referring also to FIG. 2a, FIGS. 3d-3f, and FIG. 8 in another preferred embodiment of the present invention, the catheter 270 of the present invention may further comprise a fenestration 296 along substantially the entire length of the catheter wall 272, 273 to facilitate the removal from the catheter of an enteral tube 280 having previously been placed therethrough without the need to remove the enteral tube from the patient 400. The fenestration 296 can be located along the outer diameter 272 of the catheter substantially medially between the catheter first side 276 and the catheter second side 277. In a preferred embodiment, the fenestration 296 is a membrane-like material 297 capable of tearing open sufficient to permit the enteral tube to be pulled substantially laterally through the membrane until the enteral tube 280 is without the catheter 270 (FIG. 3f).

In another preferred embodiment, the fenestration 296 comprises a slit 298 (e.g., FIG. 3d) through the entire thickness of the catheter wall thickness 272, 273 along the entire length of the catheter 270 sufficient to permit the enteral tube 280 to be pulled substantially laterally through the slit 298 until the enteral tube 280 is without the catheter 270. In one embodiment, the slit 298 is maintained in a substantially closed position with a removable strip of tape (not shown) placed over the slit 298 on the outside diameter 272 of the catheter 270. The slit 298 preferably has a width of lesser size than the outer diameter of the enteral tube 280, for example, between ¼ and ½ the size of the outer diameter of the enteral tube 280. In another embodiment, where the walls of the catheter 270 are substantially flexible, the slit width can be approximately zero (i.e., the walls on either side of of the slit are touching each other) as shown in FIG. 3e.

Figure 5A:
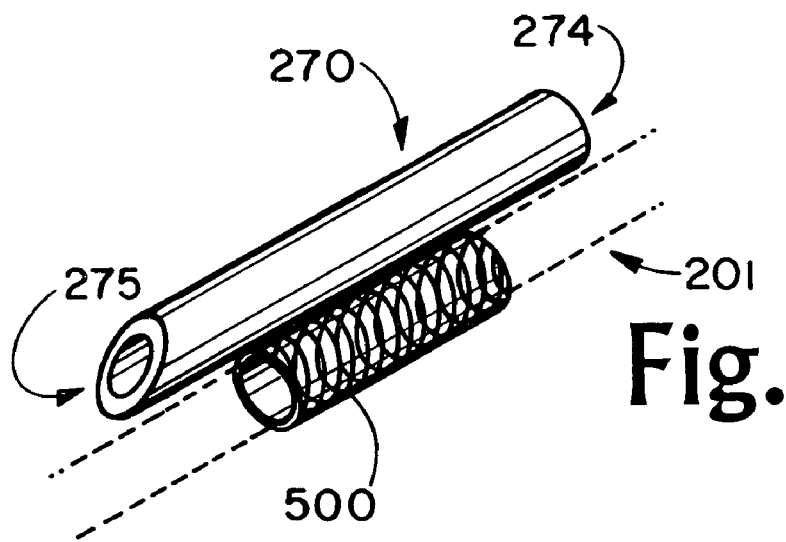
FIG. 5a shows a perspective view of a catheter according to a preferred embodiment of the present intubation invention.

The catheter 270 can be removably attached to the endotracheal tube 201. For example, referring now to FIG. 5a, in a preferred embodiment, the catheter 270 further comprises an expandable sleeve 500 connected to the outside diameter 272 of the catheter 270 for attaching the catheter to the endotracheal tube 201, the expandable sleeve 500 capable of snugly sliding over the outside diameter of the endotracheal tube. The expandable sleeve 500 can further comprise a stretchable material. The sleeve 500 can be connected along a portion of, or substantially the entire length of, the outside diameter 272 of the catheter 270, and can further comprise one or more expandable sleeves.

Figure 5B:
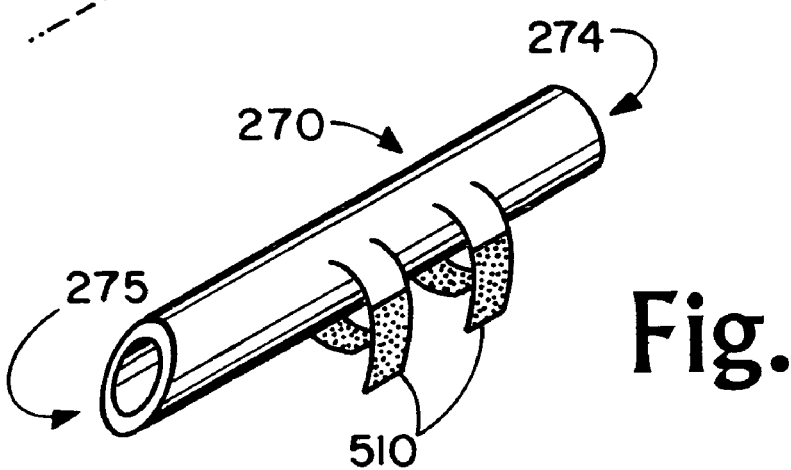
FIG. 5b shows a perspective view of a catheter according to a preferred embodiment of the present intubation invention.

In another preferred embodiment depicted generally in FIG. 5b, the expandable sleeve 500 further comprises one or more closable and reopenable closures 510 connected along the outside diameter 272 of the catheter 270, the closures 510 being capable of wrapping around the outside diameter of the endotracheal tube 201 to secure the catheter 270 to the endotracheal tube 201 or otherwise securing the catheter to the endotracheal tube.

In another preferred embodiment, the catheter 270 is fixably attached to the endotracheal tube using any number of methods known in the art, such as, for example and without limitation, extrusion molding, gluing, heat welding, chemical bonding, ring clips, tape, hook and loop fasteners, such as those sold under the VELCRO® brand, mating channels (e.g., FIG. 3g, 291, 292), mated compression fittings, fasteners, clamps (e.g., FIG. 3c) and encapsulation with shrink wrap. In one embodiment, the catheter is fixably attached to the endotracheal tube so that a seam 290 is created between the outside diameter of the catheter and the outside diameter of the endotracheal tube, the seam having a length that is adjustable.

In yet another preferred embodiment, the catheter 270 can be removably attached to the endotracheal tube 201 using a variety of methods known in the art. For example, the use of tape, hook and loop fasteners, such as those sold under the VELCRO® brand, mating channels, mated compression fittings, fasteners, clamps and the like can be employed to removably attach the catheter. For example, in a preferred embodiment, the catheter 270 and the endotracheal tube 201 contain mated linear tracks (e.g., FIG. 3g, 291, 292) for slidably attaching (or removing) the outer diameter of the catheter to the outer diameter of the endotracheal tube.

Figure 5C:
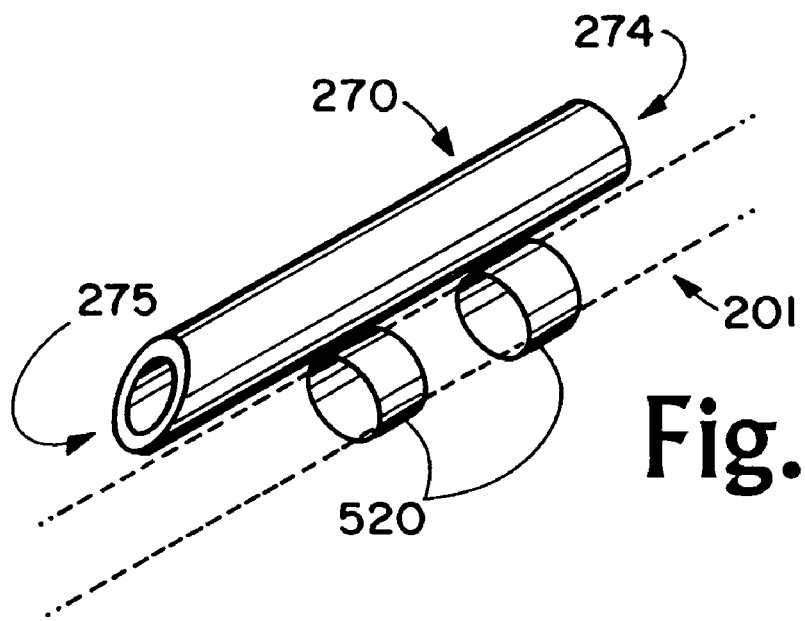
FIG. 5c shows a perspective view of a catheter according to a preferred embodiment of the present intubation invention.

Referring to FIG. 5c, the catheter 270 can also be slidably attached to the endotracheal tube, where the catheter has one or more cylindrical tubes 520 fixably attached to the anterior side of the catheter, these cylindrical tube(s) 520 being substantially co-axially aligned with each other, and the cylindrical tube(s) having a cross-sectional shape substantially similar to the cross-sectional shape of the endotracheal tube 201, an outside diameter, and an inside diameter suitable to facilitate the frictional movement of the endotracheal tube therethrough, a proximal end and a distal end. In this embodiment, the frictional fit of the endotracheal tube 201 could be accomplished in many ways known in the art, including, by way of example, rough mating surfaces; channel locks; clipping mechanisms to name a few.

The intubation device of the present invention can also be constructed in a manner that provides unitary construction. For example, the catheter and endotracheal tube can be fully integrated into unitary device (e.g., FIGS. 3b, 3d, 3e and 3f). Also, the catheter can comprise a conduit located within the wall of the endotracheal tube.

Referring to FIGS. 6a and 6b, the intubation device 200 of the present invention can also preferably further comprise: a first section 600 proximate the proximal end 210 of the endotracheal tube 201 wherein the proximal end of the catheter 274 is maintained external to the endotracheal tube 201, a second section 602 between the proximal and distal ends of the endotracheal tube wherein the catheter is maintained within the endotracheal tube, and a third section 604 toward the distal end of the endotracheal tube wherein the distal end of the catheter 275 is maintained external to the endotracheal tube 201.

In another preferred embodiment, the intubation device 200 of the present invention can be of a substantial unibody wall construction, such as depicted in, for example, FIG. 3b. In this embodiment, the device 200 comprises a first section proximate the proximal end of the endotracheal tube wherein the proximal end of the catheter is maintained within the wall of the endotracheal tube, the proximal end of the catheter being flush with the outside diameter of the endotracheal tube and remaining capable of having the enteral tube pass therethrough; a second section between the proximal and distal ends of the endotracheal tube wherein the catheter is maintained within the endotracheal tube; and a third section toward the distal end of the endotracheal tube wherein the distal end of the catheter is maintained within the wall of the endotracheal tube, the distal end of the catheter being flush with the outside diameter of the endotracheal tube and remaining capable of having the enteral tube pass therethrough.

Figure 7:
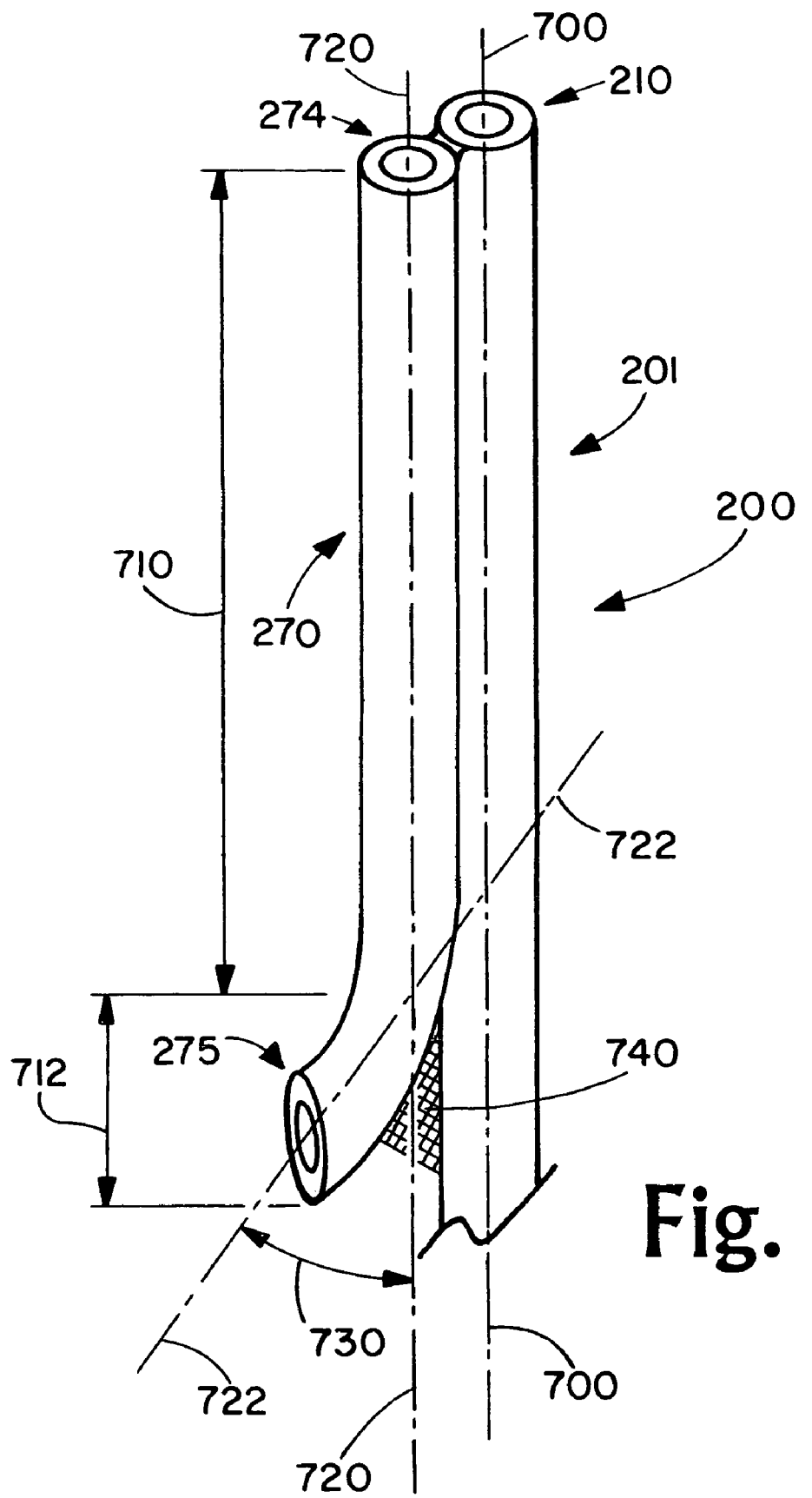
FIG. 7 illustrates a perspective top side (anterior) view of an intubation device according to another preferred embodiment of the present invention.
Figure 8:
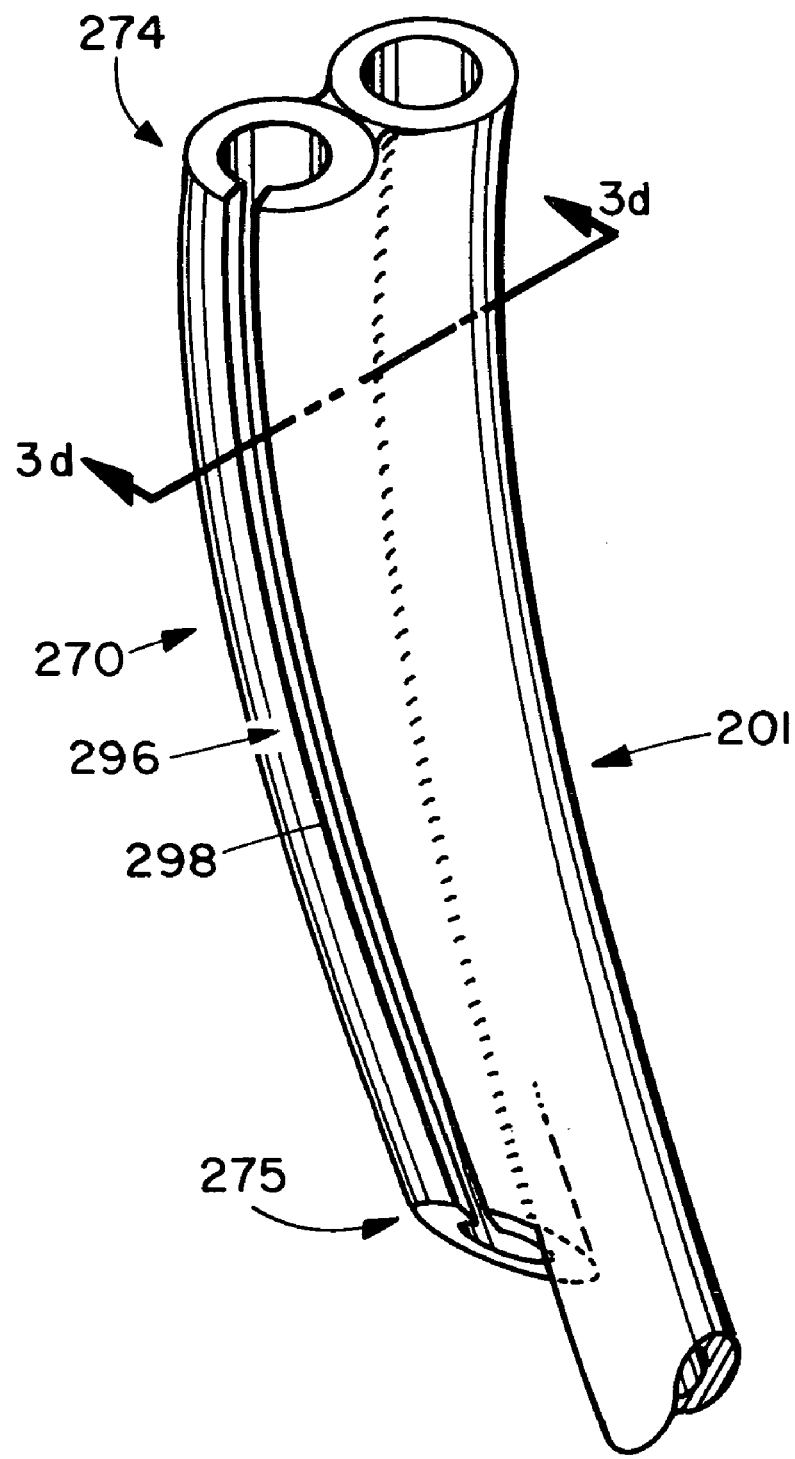
FIG. 8 illustrates a perspective top side (anterior) view of an intubation device according to another preferred embodiment of the present invention.

Referring now to FIG. 7, in another preferred embodiment, the intubation device 200 of the present invention preferably further comprises an endotracheal tube axis 700 located in the distal portion of the endotracheal tube, the endotracheal tube axis being substantially aligned with the axis of the patient's trachea when the distal end of the endotracheal tube is placed within the patient's trachea; a first catheter zone 710 located between the proximal and distal ends of the catheter, wherein the catheter has a first catheter axis 720 that is substantially parallel to the endotracheal tube axis 700; and a second catheter zone 712 located proximate the distal end 275 of the catheter 270 wherein the catheter has a second catheter axis 722 that diverges from the first catheter axis 720. In a preferred embodiment, the second catheter axis 722 diverges from the first catheter axis 720 to direct the path of the enteral tube (280 not shown) posteriorly toward the esophagus of the patient. In another preferred embodiment, the second catheter axis 722 diverges from the first catheter axis 720 to form an angle 730 between both axes (720, 722) to optimally align the distal end 275 of the catheter 270 for directing the path of the enteral tube posteriorly toward the esophagus of the patient. The angle 730 can preferably be between about 15 degrees and 60 degrees. The angle 730 can be fixed or adjustable. For example, the angle could be preconfigured in the shape of the distal end 275 of the catheter 270. Also, the angle 730 could be set by using a wedge-like (or other suitably shaped) device 740 to create or adjust the angle 730.

In another preferred embodiment of the present invention, the intubation device further comprises a malleable stylet for use in shaping the device. In one example, the endotracheal tube (and/or the catheter) further comprises a malleable stylet for use in shaping the endotracheal tube (and/or the catheter), the stylet having a distal end and a proximal end. The stylet can employ fiber optics capable of transmitting an optical image signal from the distal end of the stylet to a display device connected to the proximal end of the stylet. In a preferred embodiment, the stylet is integrated into the endotracheal tube (and/or catheter), such as by being built into the wall of the endotracheal tube (and/or catheter) (e.g., FIG. 3h, 299). Alternatively, the stylet is insertable into and removable from the inside diameter of the endotracheal tube and/or catheter.

In another preferred embodiment, the endotracheal tube (and/or catheter) further comprises one or more strands of a flexible, memory retaining material capable of being manipulated to facilitate the defining of the arcuate path or otherwise to facilitate the shaping of the endotracheal tube and/or catheter.

Additionally, the endotracheal tube of the present invention may contain a manual curvature adjustment ring 160 to likewise facilitate the defining of the arcuate path or otherwise to facilitate the shaping of the endotracheal tube 201.

In another preferred embodiment of the present invention, there is disclosed a combination medical device comprising: an endotracheal tube with a substantially circular cross-section, an outside diameter, an inside diameter, a proximal end and a distal end; and a catheter to guide the path of an enteral tube. The endotracheal tube defines an arcuate path in a first plane between its proximal end and its distal end to facilitate introduction of the tube into the trachea of a patient. The endotracheal tube employs an inflatable cuff for achieving a seal with an inner wall of the trachea of the patient positioned generally toward the distal end of the endotracheal tube, the inflatable cuff being in fluid communication with an inflation port positioned generally toward the proximal end of the endotracheal tube. The catheter has a substantially circular cross-section, an outside diameter, and an inner diameter suitable to facilitate the smooth movement of the enteral tube therethrough, and a length defined by a proximal end and a distal end. The catheter is attached to the endotracheal tube along substantially the entire length of said catheter, the proximal end of the catheter being positioned generally outside the first plane, the length of the catheter extending along only a portion of the length of the endotracheal tube. In this embodiment, the catheter defines a substantially partial-spiral path around the outside diameter of the endotracheal tube to position the distal end of the catheter in the first plane, the distal end of the catheter having a diagonal cut at the end to facilitate the introduction of the enteral tube into the esophagus of the patient. The catheter of this embodiment can also comprise a fenestration along substantially the entire length of the catheter wall to facilitate the removal from the catheter of an enteral tube having previously been placed therethrough without the need to remove the enteral tube from the patient.

The endotracheal tube of the present invention can also employ markings to assist medical personnel in ascertaining placement and positioning of the device.

In yet another preferred embodiment of the present invention, there is disclosed an endotracheal intubation device comprising:

a substantially circular cross-section, an outside diameter, an inside diameter, a proximal end, a distal end, a wall thickness defined as the space between the outside diameter and the inside diameter;

the endotracheal intubation device capable of defining an arcuate path in a first geometric plane between its proximal end and its distal end to facilitate introduction of the tube into the trachea of a patient, the arcuate path, when so defined, having a concave side and a convex side substantially opposite said concave side, the endotracheal tube, when so defined in the arcuate path, having a concave side and a convex side substantially opposite said concave side, a malleable stylet for use in shaping said endotracheal intubation device;

the stylet having a distal end and a proximal end and being integrated into said wall thickness; and an inflatable cuff for achieving a seal with an inner wall of the trachea of the patient positioned generally toward the distal end of said endotracheal intubation device, the inflatable cuff being in fluid communication with an inflation port positioned generally toward the proximal end of said endotracheal tube.

In this embodiment, the stylet can further comprise one or more strands of a flexible, memory retaining material capable of being manipulated to facilitate the defining of the arcuate path. Additionally, if desired, this intubation device can employ integrated fiber optics capable of transmitting an optical image signal from the distal end to a display device.

In yet another preferred embodiment of the present invention, there is described a method of intubating a patient comprising the steps of: (a) providing an intubation device in accordance with embodiments of the present invention; (b) inserting into the oral cavity of a patient the intubation device oriented such that the distal end of the endotracheal tube enters first; (c) orienting the distal end of the endotracheal tube with the patient's trachea; (d) inserting the distal end of the endotracheal tube into the patient's trachea; (e) inflating the inflatable cuff by administering a source of air into the inflation port; and ventilating the patient through the endotracheal tube. A preferred embodiment includes the additional step of directing a desired enteral tube into the proximal end of the catheter, through the catheter, out the distal end of the catheter and into the desired location of the patient Another preferred embodiment of this method includes the additional step of removing the intubation device without removing said enteral tube from said desired location within the patient.

When the catheter of the intubation device of the present invention includes the fenestration feature, a preferred embodiment of the present inventive method can also include the additional steps of: deflating the inflatable cuff of the endotracheal tube; maintaining the enteral tube in its desired location while withdrawing the intubation device from the patient's oral cavity; and maintaining the enteral tube in its desired location while directing the enteral tube through the fenestration.

When the catheter of the intubation device of the present invention includes an integrated, malleable stylet for use in shaping the intubation device, a preferred embodiment of the present inventive method can also include the additional step of: shaping the intubation device prior to inserting the device into the oral cavity of a patient so that the shape of the intubation device facilitates the insertion of the device into the oral cavity of the patient.

When the catheter of the intubation device of the present invention includes an integrated array of fiber optics capable of transmitting an optical image signal from the distal end of the device to a display device external to the patient, a preferred embodiment of the present inventive method can also include the additional step of: viewing the display of the fiber optics image signal on the display device while inserting the intubation device into the patient to facilitate placement of the intubation device.

The conduits may individually include reinforcement that inhibits collapse of the conduit. However, the coupling of the primary tracheal conduit with the auxiliary gastric conduit serves also to reinforce the coupled conduits to prevent collapse from, e.g., patient biting.

The following represents an exemplary list of references.

| U.S. Patent References | | |
| --- | --- | --- |
| 1. | Angel - US 2004/0000314 A1 | |
| 2. | Fortuna - US 2004/0020491 A1 | |
| 3. | Ranzinger - US 2003/0183234 A1 | |
| 4. | Sniadach - US 2003/0062039 A1 | |
| 5. | Alfery - 6,729,325 | |
| 6. | Klepper - 6,460,540 | |
| 7. | Bowden et al. - 6,374,827 | |
| 8. | Frass et al. - 5,499,625 | |
| 9. | Insler, et al. - 5,588,424 | |
| 10. | Price - 5,353,787 | |
| 11. | Price - 5,253,643 | |
| 12. | Peckham - 5,143,062 | |
| 13. | White, et al. - 4,774,945 | |
| 14. | McGrail - 4,584,998 | |
| 15. | Scarberry - 4,351,330 | |
| 16. | Dryden - 4,256,099 | |
| 17. | Scarberry - 4,231,365 | |
| 18. | Elam - 4,090,518 | |
| 19. | Sheridan - 3,625,793 | |
| Non-U.S. Patent References | | |
| 20. | Ranzinger - JPO abstract 2002-315832 | |
| 21. | Frankel - EPO 0 230 790 | |
| 22. | Skoljarev - DE19533615 - English language abstract. | |

All references referred to herein are incorporated herein by reference. While the apparatus and methods of this invention have been described in terms of preferred embodiments, it will be apparent to those of skill in the art that variations may be applied to the process and system described herein without departing from the concept and scope of the invention. All such similar substitutes and modifications apparent to those skilled in the art are deemed to be within the scope and concept of the invention. Those skilled in the art will recognize that the method and apparatus of the present invention has many applications, and that the present invention is not limited to the representative examples disclosed herein. Moreover, the scope of the present invention covers conventionally known variations and modifications to the system components described herein, as would be known by those skilled in the art. While the apparatus and methods of this invention have been described in terms of preferred or illustrative embodiments, it will be apparent to those of skill in the art that variations may be applied to the process described herein without departing from the concept and scope of the invention. All such similar substitutes and modifications apparent to those skilled in the art are deemed to be within the scope and concept of the invention as it is set out in the following claims.

What is claimed is:

1. A combination intubation device comprising:
an endotracheal tube for ventilation of a patient's lungs, said endotracheal tube having an outside diameter, an inside diameter defining an endotracheal ventilation lumen, a proximal end and a distal end,
said endotracheal tube capable of defining an arcuate path in a first geometric plane between its proximal end and its distal end to facilitate introduction of said endotracheal tube into the trachea of the patient,
said endotracheal tube having a wall thickness defined as the space between said outside diameter and said inside diameter,
said arcuate path, when so defined, having a concave side and a convex side substantially opposite said concave side,
said endotracheal tube, when so defined in said arcuate path, having a concave side and a convex side substantially opposite said concave side,
said outside diameter of said endotracheal tube having a first edge along the concave side of said defined arcuate path and a second edge along the convex side of said defined arcuate path,
an inflatable cuff for achieving a seal, when inflated, with said endotracheal tube outside diameter and an inner wall of the trachea of the patient when the distal end of said endotracheal tube is inserted into the patient's trachea, said cuff being positioned generally toward the distal end of said endotracheal tube,
said inflatable cuff being in fluid communication with an inflation port positioned generally toward the proximal end of said endotracheal tube, and
a catheter capable of receiving an enteral tube therethrough and guiding the path of the enteral tube, said catheter comprising:
a length defined by a proximal end and a distal end,
a catheter first side capable of being attached to said endotracheal tube along the length of said catheter, the length of said catheter extending along only a portion of the length of said endotracheal tube,
a catheter second side substantially opposite said catheter first side,
an outside diameter,
an inside diameter suitable to facilitate the movement of the enteral tube therethrough, said inside diameter defining an internal catheter conduit space between said catheter proximal and distal ends, the enteral tube having an outside diameter of sufficient size to permit movement of the enteral tube through said internal catheter conduit space,
a catheter proximal end opening at said catheter proximal end for receiving the enteral tube into said internal catheter conduit space,
a catheter distal end opening at said distal end to permit the enteral tube to enter the esophagus of the patient, and
a catheter wall thickness defined as the space between said outside diameter and said inside diameter,
said distal end of said catheter being positioned proximate the opening of the patient's esophagus when the distal end of said endotracheal tube is inserted into the patient's trachea.

2. The device of claim 1 wherein said endotracheal tube is constructed of a flexible, generally transparent material.

3. The device of claim 1 wherein said first side of said catheter is attached to said endotracheal tube along substantially the entire length of said catheter.

4. The device of claim 1 wherein said catheter is constructed of a flexible, generally transparent material.

5. The device of claim 1 wherein the enteral tube is an orogastric tube.

6. The device of claim 1 wherein the distal end of said catheter is positioned to direct the path of the enteral tube posteriorly toward the esophagus of the patient after the enteral tube exits from said catheter distal end opening.

7. The device of claim 1 wherein the distal end of said catheter is positioned to direct the path of the enteral tube into the esophageal limb of the patient.

8. The device of claim 1 wherein said distal end of said catheter has a diagonal cut at said end to facilitate the introduction of the enteral tube into the esophagus of the patient after the enteral tube exits from said catheter distal end opening.

9. The device of claim 1 wherein the proximal end of said catheter is positioned generally within said first plane and the distal end of said catheter is positioned generally within said first plane.

10. The device of claim 1 wherein the proximal end of said catheter is positioned generally within said first plane and the distal end of said catheter is positioned generally outside of said first plane.

11. The device of claim 1 wherein the proximal end of said catheter is positioned generally outside of said first plane and the distal end of said catheter is positioned generally within said first plane.

12. The device of claim 1 wherein the proximal end of said catheter is positioned generally outside of said first plane and the distal end of said catheter is positioned generally outside of said first plane.

13. The device of claim 1 wherein said arcuate path concave side is generally pointing in a direction away from the patient's vertebra when said endotracheal tube is inserted into the patient, and said arcuate path convex side is generally pointing toward the patient's vertebra when said endotracheal tube is inserted into the patient, said outside diameter of said endotracheal tube having a first edge along the first side of said arcuate path and a second edge along the second side of said arcuate path.

14. The device of claim 13 wherein the proximal end of said catheter is positioned generally within said first plane, said catheter defining a substantially linear path along the second edge of the outside diameter of said endotracheal tube.

15. The device of claim 13 wherein the proximal end of said catheter is positioned generally outside said first plane, said catheter defining a substantially partial-spiral path around the outside diameter of said endotracheal tube to position said distal end of said catheter in said first plane proximate the second edge of the outside diameter of said endotracheal tube.

16. The device of claim 15 wherein said substantially partial spiral path traverses approximately 90-degrees along the outside diameter of said endotracheal tube.

17. The device of claim 15 wherein the proximal end of said catheter is side-by-side said endotracheal tube in a second plane substantially normal to said first plane.

18. The device of claim 17 wherein the distal end of said catheter is side-by-side said endotracheal tube in a second plane substantially normal to said first plane.

19. The device of claim 13 wherein said catheter further comprises a fenestration along substantially the entire length of the catheter wall to facilitate the removal from said catheter of an enteral tube having previously been placed therethrough without the need to remove the enteral tube from the patient.

20. The device of claim 19 wherein said fenestration is located along said outer diameter of said catheter substantially medially between said catheter first side and said catheter second side.

21. The device of claim 19 wherein said fenestration is a membrane-like material capable of tearing open sufficient to permit said enteral tube to be pulled substantially laterally through said membrane until said enteral tube is without said catheter.

22. The device of claim 19 wherein said fenestration comprises a slit through the entire thickness of said catheter wall thickness along the entire length of said catheter sufficient to permit said enteral tube to be pulled substantially laterally through said slit until said enteral tube is without said catheter.

23. The device of claim 22 wherein said slit is maintained in a substantially closed position with a removable strip of tape placed over said slit on the outside diameter of said catheter.

24. The device of claim 22 wherein said slit has a width of lesser size than the outer diameter of said enteral tube.

25. The device of claim 24 wherein said slit has a width of between ¼ and ½ the size of the outer diameter of said enteral tube.

26. The device of claim 13 further comprising:

an endotracheal tube axis located in the distal portion of said endotracheal tube, said endotracheal tube axis being substantially aligned with the axis of the patient's trachea when said distal end of said endotracheal tube is placed within the patient's trachea, a first catheter zone located between the proximal and distal ends of said catheter, wherein said catheter has a first catheter axis that is substantially parallel to said endotracheal tube axis, and a second catheter zone located proximate the distal end of said catheter wherein said catheter has a second catheter axis that diverges from said first catheter axis.

27. The device of claim 26 wherein said second catheter axis diverges from said first catheter axis to direct the path of the enteral tube posteriorly toward the esophagus of the patient.

28. The device of claim 26 wherein said second catheter axis diverges from said first catheter axis to form an angle between both said axes to optimally align the distal end of said catheter for directing the path of the enteral tube posteriorly toward the esophagus of the patient.

29. The device of claim 28 wherein said angle is between about 15 degrees and 60 degrees.

30. The device of claim 1 wherein the proximal end of said catheter is positioned generally outside said first plane, said catheter defining a substantially helical path around the outside diameter of said endotracheal tube.

31. The device of claim 1 wherein the proximal end of said catheter is positioned generally within said first plane, said catheter defining a substantially helical path around the outside diameter of said endotracheal tube.

32. The device of claim 1 wherein said catheter further comprises an expandable sleeve connected to the outside diameter of said catheter for attaching said catheter to said endotracheal tube, said expandable sleeve capable of snugly sliding over the outside diameter of said endotracheal tube.

33. The device of claim 32 wherein said expandable sleeve further comprises a stretchable material.

34. The device of claim 32 wherein said expandable sleeve is connected along a portion of the outside diameter of said catheter.

35. The device of claim 32 wherein said expandable sleeve is connected along substantially the entire length of the outside diameter of said catheter.

36. The device of claim 32 wherein said expandable sleeve further comprises a plurality of expandable sleeves connected along the outside diameter of said catheter.

37. The device of claim 32 wherein said expandable sleeve further comprises one or more closable and reopenable closures connected along the outside diameter of said catheter,
said one or more closures being capable of wrapping around the outside of said endotracheal tube diameter to secure said catheter to said endotracheal tube.

38. The device of claim 1 wherein said catheter is fixably attached to said endotracheal tube.

39. The device of claim 38 wherein said catheter is fixably attached to said endotracheal tube using one or more attachment methods selected from group consisting of: extrusion molding, gluing, heat welding, chemical bonding, ring clips, tape, hook and loop fasteners, mating channels, mated compression fittings, fasteners, clamps and encapsulation with shrink wrap.

40. The device of claim 38 wherein said catheter is fixably attached to said endotracheal tube so that a seam is created between the outside diameter of said catheter and the outside diameter of said endotracheal tube, said seam having a length that is adjustable.

41. The device of claim 1 wherein said catheter is removably attached to said endotracheal tube.

42. The device of claim 41 wherein said catheter and said endotracheal tube contain mated linear tracks for slidably attaching the outer diameter of said catheter to the outer diameter of said endotracheal tube.

43. The device of claim 41 wherein said catheter is removably attached to said endotracheal tube using one or more attachment methods selected from group consisting of: ring clips, mated compression fittings, fasteners, and clamps.

44. The device of claim 1 wherein said catheter is slidably attached to said endotracheal tube,
said catheter having one or more cylindrical tubes fixably attached to the anterior side of said catheter,
said one or more cylindrical tubes being substantially coaxially aligned with each other,
said one or more cylindrical tubes having a cross-sectional shape substantially similar to the cross-section of said endotracheal tube, an outside diameter, and an inside diameter suitable to facilitate the frictional movement of said endotracheal tube therethrough, a proximal end and a distal end.

45. The device of claim 1 further comprising:
a first section proximate the proximal end of said endotracheal tube wherein the proximal end of said catheter is maintained external to said endotracheal tube,
a second section between the proximal and distal ends of said endotracheal tube wherein said catheter is maintained within said endotracheal tube, and
a third section toward the distal end of said endotracheal tube wherein the distal end of said catheter is maintained external to said endotracheal tube.

46. The device of claim 1 further comprising:
a first section proximate the proximal end of said endotracheal tube wherein the proximal end of said catheter is maintained within the wall of said endotracheal tube, said proximal end of said catheter being flush with the outside diameter of said endotracheal tube and remaining capable of having the enteral tube pass therethrough,
a second section between the proximal and distal ends of said endotracheal tube wherein said catheter is maintained within said endotracheal tube, and
a third section toward the distal end of said endotracheal tube wherein the distal end of said catheter is maintained within the wall of said endotracheal tube, said distal end of said catheter being flush with the outside diameter of said endotracheal tube and remaining capable of having the enteral tube pass therethrough.

47. The device of claim 1 wherein said catheter is a conduit located within the wall of said endotracheal tube.

48. The device of claim 1 wherein said endotracheal tube further comprises a malleable stylet for use in shaping said endotracheal tube,
said stylet having a distal end and a proximal end.

49. The device of claim 48 wherein said stylet employs fiber optics capable of transmitting an optical image signal from said distal end of said stylet to a display device connected to said proximal end of said stylet.

50. The device of claim 48 wherein said stylet is integrated into said endotracheal tube.

51. The device of claim 48 wherein said stylet is built into said wall of said endotracheal tube.

52. The device of claim 48 wherein said stylet is insertable into and removable from said inside diameter of said endotracheal tube.

53. The device of claim 1 wherein said endotracheal tube further comprises one or more strands of a flexible, memory retaining material capable of being manipulated to facilitate the defining of said arcuate path.

54. The device of claim 1 wherein said catheter further comprises a malleable stylet for use in shaping said catheter tube.

55. The device of claim 54 wherein said stylet is integrated into said catheter.

56. The device of claim 54 wherein said stylet is built into said wall of said catheter.

57. The device of claim 54 wherein said stylet is insertable into and removable from said inside diameter of said catheter.

58. The device of claim 1 wherein said catheter further comprises one or more strands of a flexible, memory retaining material capable of being manipulated to facilitate the shaping of said catheter.

59. The device of claim 1 wherein said endotracheal tube and said catheter further comprise one or more strands of a flexible, memory retaining material capable of being manipulated to facilitate the shaping of said endotracheal tube and said catheter.

60. The device of claim 1 wherein said endotracheal tube contains markings to assist medical personnel in ascertaining placement and positioning of the device.

61. The device of claim 1 wherein said endotracheal tube has a substantially circular cross-section.

62. The device of claim 1 wherein said catheter has a substantially circular cross-section.

63. A combination medical device comprising:
an endotracheal tube for use in ventilating a patient's lungs,
said endotracheal tube having an outside diameter, an inside diameter defining an endotracheal ventilation lumen, a proximal end and a distal end,
said endotracheal tube capable of defining an arcuate path in a first geometric plane between its proximal end and its distal end to facilitate introduction of said endotracheal tube into the trachea of the patient,
an inflatable cuff for achieving a seal, when inflated, with said endotracheal tube outside diameter and an inner wall of the trachea of the patient when the distal end of said endotracheal tube is inserted into the patient's trachea, said cuff being positioned generally toward the distal end of said endotracheal tube, said inflatable cuff being in fluid communication with an inflation port positioned generally toward the proximal end of said endotracheal tube, and a catheter capable of receiving an enteral tube therethrough and guiding the path of the enteral tube, said catheter comprising:

a length defined by a proximal end and a distal end, an outside diameter, an inside diameter suitable to facilitate the movement of the enteral tube therethrough, said inside diameter defining an internal catheter conduit space between said catheter proximal and distal ends, a catheter proximal end opening at said catheter proximal end for receiving the enteral tube into said internal catheter conduit space, a catheter distal end opening at said distal end to permit the enteral tube to enter the esophagus of the patient, and said catheter being attached to said endotracheal tube along substantially the entire length of said catheter, said proximal end of said catheter being positioned generally outside said first plane, the length of said catheter extending along only a portion of the length of said endotracheal tube, said catheter defining a substantially partial-spiral path around the outside diameter of said endotracheal tube to position said distal end of said catheter in said first plane, said distal end of said catheter having a diagonal cut at said end and being positioned proximate the opening of the patient's esophagus when the distal end of said endotracheal tube is inserted into the patient's trachea.

64. The combination of claim 63 wherein said catheter further comprises a fenestration along substantially the entire length of the catheter wall to facilitate the removal from said catheter of an enteral tube having previously been placed therethrough without the need to remove the enteral tube from the patient.

65. The device of claim 63 wherein said endotracheal tube has a substantially circular cross-section.

66. The device of claim 63 wherein said catheter has a substantially circular cross-section.

67. A method of intubating a patient comprising:

(a) providing a combination intubation device, said intubation device comprising, an endotracheal tube for ventilation of the patient's lungs, said endotracheal tube having an outside diameter, an inside diameter defining an endotracheal ventilation lumen, a proximal end and a distal end, said endotracheal tube capable of defining an arcuate path in a first geometric plane between its proximal end and its distal end to facilitate introduction of said endotracheal tube into the trachea of the patient, said endotracheal tube having a wall thickness defined as the space between said outside diameter and said inside diameter, said arcuate path, when so defined, having a concave side and a convex side substantially opposite said concave side, said endotracheal tube, when so defined in said arcuate path, having a concave side and a convex side substantially opposite said concave side, said outside diameter of said endotracheal tube having a first edge along the concave side of said defined arcuate path and a second edge along the convex side of said defined arcuate path, an inflatable cuff for achieving a seal, when inflated, with said endotracheal tube outside diameter and an inner wall of the trachea of the patient, said cuff being positioned generally toward the distal end of said endotracheal tube, said inflatable cuff being in fluid communication with an inflation port positioned generally toward the proximal end of said endotracheal tube, and a catheter capable of receiving an enteral tube therethrough and guiding the path of the enteral tube, said catheter comprising:

a length defined by a proximal end and a distal end, a catheter first side capable of being attached to said endotracheal tube along the length of said catheter, the length of said catheter extending along only a portion of the length of said endotracheal tube, a catheter second side substantially opposite said catheter first side, an outside diameter, an inside diameter suitable to facilitate the movement of the enteral tube therethrough said inside diameter defining an internal catheter conduit space between said catheter proximal and distal ends, the enteral tube having an outside diameter of sufficient size to permit movement of the enteral tube through said internal catheter conduit space, a catheter proximal end opening at said catheter proximal end for receiving the enteral tube into said internal catheter conduit space, a catheter distal end opening at said distal end to permit the enteral tube to enter the esophagus of the patient, and a catheter wall thickness defined as the space between said outside diameter and said inside diameter, said distal end of said catheter being positioned proximate the opening of the patient's esophagus when the distal end of said endotracheal tube is inserted into the patient's trachea;

(b) inserting into the oral cavity of a patient said intubation device oriented such that the distal end of said endotracheal tube enters first;

(c) orienting said distal end of said endotracheal tube with the patient's trachea;

(d) inserting said distal end of said endotracheal tube into the patient's trachea;

(e) inflating said inflatable cuff by administering a source of air into said inflation port; and (f) ventilating the patient through said endotracheal tube ventilation lumen.

68. The method of claim 67 comprising the additional step of:

(g) directing a desired enteral tube into said catheter proximal end opening, through said internal catheter conduit space, out said catheter distal end opening and into the patient's esophagus or other desired location of the patient that is accessed via the patient's esophagus.

69. The method of claim 68 comprising the additional step of removing the intubation device without removing said enteral tube from within the patient.

70. The method of claim 68 wherein said catheter of said intubation device further comprises a fenestration along substantially the entire length of the catheter wall to facilitate the removal of an enteral tube having previously been placed therethrough without the need to remove the enteral tube from the patient, said fenestration also facilitating the removal of said endotracheal tube and said catheter without the need to remove said enteral tube previously placed within the patient through said catheter, said method comprising the additional steps of:

deflating said inflatable cuff;

maintaining said enteral tube in its desired location while withdrawing said intubation device from the patient's oral cavity; and maintaining said enteral tube in its desired location while directing said enteral tube through said fenestration.

71. The method of claim 67 wherein said intubation device further comprises an integrated, malleable stylet for use in shaping said intubation device, said method comprising the additional step of:

shaping said intubation device prior to inserting said device into the oral cavity of a patient so that said shape of said intubation device facilitates the insertion of said device into the oral cavity of the patient.

72. The method of claim 67 wherein said intubation device further comprises an integrated array of fiber optics capable of transmitting an optical image signal from said distal end of said device to a display device external to the patient, said method comprising the additional step of:

Viewing the display of said fiber optics image signal on said display device while inserting said intubation device into the patient to facilitate placement of said intubation device.

73. The method of claim 67 comprising the additional steps of inserting a stylet into the inside diameter of said endotracheal tube and shaping said endotracheal tube to facilitate placement of said intubation device into the patient.

74. The method of claim 67 wherein said endotracheal tube has a substantially circular cross-section.

75. The method of claim 67 wherein said catheter has a substantially circular cross-section.

* * * * *